(12) United States Patent
Thonnard

(10) Patent No.: US 6,627,728 B1
(45) Date of Patent: Sep. 30, 2003

(54) COMPOUNDS FROM MORAXELLA CATARRHALIS

(75) Inventor: Joelle Thonnard, Gembloux (BE)

(73) Assignee: SmithKline Beecham Biologicals s.a., Rixensart (BE)

( * ) Notice: Subject to any disclaimer, the term of this patent is extended or adjusted under 35 U.S.C. 154(b) by 0 days.

(21) Appl. No.: 09/700,336

(22) PCT Filed: May 7, 1999

(86) PCT No.: PCT/EP99/03254

§ 371 (c)(1),
(2), (4) Date: Jul. 16, 2001

(87) PCT Pub. No.: WO99/58682

PCT Pub. Date: Nov. 18, 1999

(30) Foreign Application Priority Data

May 12, 1998 (GB) ............................................. 9810195
Mar. 8, 1999 (GB) ............................................. 9905308

(51) Int. Cl.⁷ ..................... A61K 38/00; A61K 39/395; G01N 33/53; C12P 21/08; C07K 16/00
(52) U.S. Cl. ................. 530/300; 424/130.1; 424/134.1; 424/150.1; 424/185.1; 424/251.1; 435/7.2; 435/7.32; 530/387.3; 530/388.2
(58) Field of Search .......................... 424/130.1, 134.1, 424/150.1, 185.1, 251.1; 435/7.2, 7.32; 530/300, 387.3, 388.2

(56) References Cited

FOREIGN PATENT DOCUMENTS

| WO | WO 93/03761 | 3/1993 |
|---|---|---|
| WO | WO 95/09025 | 4/1995 |
| WO | WO 96/34960 | 11/1996 |
| WO | WO 97/32980 | 9/1997 |
| WO | WO 97/41731 | 11/1997 |
| WO | WO 98/06851 | 2/1998 |

OTHER PUBLICATIONS

Kyd et al, Vaccine 18, 200, 398–406.*
Samukawa et al, Journal of Infectious Diseases, 200, 181:1842–1845.*
Chen et al, Infection and Immunity, Jun. 1996, p. 1900–1905.*
Gu et al, Infection and Immunity, May 1998, p. 1891–1897.*
Hu et al, Infection Immunity, Sep. 2000, p. 4980–4985.*
Sarwar et al, Infection and Immunity, Mar. 1992, p. 804–809.*
Murphy et al, Infection and Immunity, Oct. 1999, p. 2938–2941.*
Kaneko, T., et al. AC S75595, EMBL Database, Apr. 25, 1997, Heidelberg.
Fraser C. et al: AC B70125, EMBL Database, Feb. 13, 1998, Heidelberg.

* cited by examiner

Primary Examiner—Lynette R. F. Smith
Assistant Examiner—Vanessa L Ford
(74) Attorney, Agent, or Firm—Jeffrey A. Sutton; Eric A. Meade

(57) ABSTRACT

The invention provides BASB010 polypeptides and polynucleotides encoding BASB010 polypeptides and methods for producing such polypeptides by recombinant techniques. Also provided are diagnostic, prophylactic and therapeutic uses.

6 Claims, 19 Drawing Sheets

Figure 2A

Identity to SeqID No:1 is indicated by a dot.

```
              *         20         *         40         *
Seqid1 : TTGTCTTTTGTTTCTATCGCTATTTTTACTGTATCAGTAGCGGCTATATT :  50
Seqid3 : ..............................A................. :  50
Seqid5 : ................................................. :  50

60        *         80         *        100
Seqid1 : TATCCCCTCAACGGCATTTGCTGCGTTTGAGCTTGGTGGCACACCGACCA : 100
Seqid3 : ................................................. : 100
Seqid5 : ................................................. : 100

*        120         *        140         *
Seqid1 : ATCTTGCGTTATTGATTTTTTTATTTGTTTATCTTTAGTCGTGTCATTT : 150
Seqid3 : ................................................. : 150
Seqid5 : ................................................. : 150

160         *        180         *        200
Seqid1 : TTATGCTCTATTTCTGAAGCGACATTGTTAACCATGACACCTTCTTATAT : 200
Seqid3 : ................................................. : 200
Seqid5 : ................................................. : 200

*        220         *        240         *
Seqid1 : TGACACGCTTGAAGAAGATAATCCCAAAGGAGCGGCACTGCTTAAGAGTG : 250
Seqid3 : ...T............................................. : 250
Seqid5 : ................................................. : 250

260         *        280         *        300
Seqid1 : TGAAAGTTGACCACATCGAAAAATCAATTTCAGCAATTTTAACACTCAAT : 300
Seqid3 : ................................................. : 300
```

Figure 2B

Identity to SeqID No:1 is indicated by a dot.

```
Seqid5  : .................................................. :  300

*         320         *         340         *
Seqid1  : ACTGTCGCCCATACATTAGGTTCGCTTGGTGCAGGCGCGCAAGCAGTGAT : 350
Seqid3  : .................................................. : 350
Seqid5  : .................................................. : 350

360         *         380         *         400
Seqid1  : CGTTTTTGGTAATGCATGGTTTGGGGTATTTAGCGGTGTGATGACTTTGA : 400
Seqid3  : .................................................. : 400
Seqid5  : .................................................. : 400

*         420         *         440         *
Seqid1  : TTATTTTGATTGGCACAGAAATTATCCCAAAAACCATCGGAACGGTATAT : 450
Seqid3  : .................................................. : 450
Seqid5  : .................................................. : 450

460         *         480         *         500
Seqid1  : TGGCGACGATTTGCTATGCCTGTGGCGTATTATGTGCGTACAATCAATGT : 500
Seqid3  : .................................................. : 500
Seqid5  : .................................................. : 500

*         520         *         540         *
Seqid1  : GGCATTATTGCCCGTTATTTGGGTGACTGAAAAAATTTCACGCATGTTGA : 550
Seqid3  : .................................................. : 550
Seqid5  : .................................................. : 550

560         *         580         *         600
Seqid1  : CTCGTGGCAATCAAGAAATTGGTTTTAATCGCCATGAGTTTTGGCACTT : 600
Seqid3  : .................................................. : 600
Seqid5  : .................................................. : 600
```

Figure 2C

```
                  *         620         *         640         *
Seqid1 : GCCAATCAAGGGGAAAGCTTGGGGCAGATGAGCGAGATGGAAACTCGTAT :  650
Seqid3 : ................................................. :  650
Seqid5 : ................................................. :  650

660         *         680         *         700
Seqid1 : TATCAAAAACTCTTTGGCATTGGGCATGATTAATGTAGAAGACATTTTGA :  700
Seqid3 : ................................................. :  700
Seqid5 : ................................................. :  700

*         720         *         740         *
Seqid1 : CGCCTCGTTCGGTCGTTAGTGCGTTTGATGAAAATATGACGGTAGGCGAT :  750
Seqid3 : ................................................. :  750
Seqid5 : ................................................. :  750

760         *         780         *         800
Seqid1 : GTCTTTGCCAGCTATCCCAAACTACCTTTTTCTCGTTTTCCAATCTTTGA :  800
Seqid3 : ................................................. :  800
Seqid5 : ................................................. :  800

*         820         *         840         *
Seqid1 : TGAAGATTTGGATAATGCCACAGGGTTTATATTAAAATCCGATTTACTGA :  850
Seqid3 : ................................................. :  850
Seqid5 : ................................................. :  850

860         *         880         *         900
Seqid1 : TCGCTAAGGCAAATCAAGAAATTCATACACCCATCAAGCAATTTCGGCGT :  900
Seqid3 : ................................G................ :  900
Seqid5 : ................................................. :  900

```
Seqid1 : GATATCAACTTTGTATTTGCCAAAATGAAACTATTTGATTTGTTGGATTT :  950
Seqid3 : .................................................. :  950
Seqid5 : .................................................. :  950

960         *         980         *        1000
Seqid1 : GATGTTAAAAGAGCAAGTTCACATCGCTTTAGCGGTAGGAGAATTTGGTG : 1000
Seqid3 : .................................................. : 1000
Seqid5 : .................................................. : 1000

*        1020         *        1040         *
Seqid1 : AGGTTAAAGGATTGGTGAGCTTAGAAGATGTGCTAGAAACCTTGCTTGGT : 1050
Seqid3 : .................................................. : 1050
Seqid5 : .................................................. : 1050

1060         *        1080         *        1100
Seqid1 : CTTGAGATTGTTGATGAATTTGACCGTGTTGATGATATGCAGATTTTAGC : 1100
Seqid3 : .................................................. : 1100
Seqid5 : .................................................. : 1100

*        1120         *        1140         *
Seqid1 : ACGCCAACTCATGGATAAACGCATGGCACGCTTGGGGGCAAAACTAGAAG : 1150
Seqid3 : .................................................. : 1150
Seqid5 : .................................................. : 1150

1160              *
Seqid1 : AAGATGCACCGTTTGATGAAAAGTAG : 1176
Seqid3 : .......................... : 1176
Seqid5 : .......................... : 1176
```

Figure 3A

Identity to SeqID No:2 is indicated by a dot.

```
                *         20          *         40            *
Seqid2 : MSFVSIAIFTVSVAAIFIPSTAFAAFELGGTPTNLALLIFFICLSLVVSF :  50
Seqid4 : ........Y......................................... :  50
Seqid6 : .................................................. :  50

60          *         80          *         100
Seqid2 : LCSISEATLLTMTPSYIDTLEEDNPKGAALLKSVKVDHIEKSISAILTLN : 100
Seqid4 : ...............V.................................. : 100
Seqid6 : .................................................. : 100

*         120         *         140           *
Seqid2 : TVAHTLGSLGAGAQAVIVFGNAWFGVFSGVMTLIILIGTEIIPKTIGTVY : 150
Seqid4 : .................................................. : 150
Seqid6 : .................................................. : 150

160         *         180         *         200
Seqid2 : WRRFAMPVAYYVRTINVALLPVIWVTEKISRMLTRGNQEIGFNRHEFLAL : 200
Seqid4 : .................................................. : 200
Seqid6 : .................................................. : 200

*         220         *         240           *
Seqid2 : ANQGESLGQMSEMETRIIKNSLALGMINVEDILTPRSVVSAFDENMTVGD : 250
Seqid4 : .................................................. : 250
Seqid6 : .................................................. : 250

260         *         280         *         300
Seqid2 : VFASYPKLPFSRFPIFDEDLDNATGFILKSDLLIAKANQEIHTPIKQFRR : 300
```

Figure 3B

```
                                                               *
Seqid4 : ..............................................C..  : 300
Seqid6 : ..................................................  : 300

*         320          *         340           *
Seqid2 : DINFVFAKMKLFDLLDLMLKEQVHIALAVGEFGEVKGLVSLEDVLETLLG  : 350
Seqid4 : ..................................................  : 350
Seqid6 : ..................................................  : 350

360            *         380           *
Seqid2 : LEIVDEFDRVDDMQILARQLMDKRMARLGAKLEEDAPFDEK  : 391
Seqid4 : .........................................  : 391
Seqid6 : .........................................  : 391
```

COMPOUNDS FROM MORAXELLA CATARRHALIS

This application is a 371 of PCT/EP99/03254 filed May 7, 1999.

FIELD OF THE INVENTION

This invention relates to polynucleotides, (herein referred to as "BASB010 polynucleotide(s)"), polypeptides encoded by them (referred to herein as "BASB010" or "BASB010 polypeptide(s)"), recombinant materials and methods for their production. In another aspect, the invention relates to methods for using such polypeptides and polynucleotides, including vaccines against bacterial infections. In a further aspect, the invention relates to diagnostic assays for detecting infection of certain pathogens.

BACKGROUND OF THE INVENTION

*Moraxella catarrhalis* (also named *Branhamella catarrhalis*) is a Gramnegative bacteria frequently isolated from the human upper respiratory tract. It is responsible for several pathologies the main ones being otitis media in infants and children, and pneumonia in elderlies. It is also responsible of sinusitis, nosocomial infections and less frequently of invasive diseases.

Otitis media is an important childhood disease both by the number of cases and its potential sequelae. More than 3.5 millions cases are recorded every year in the United States, and it is estimated that 80% of the children have experienced at least one episode of otitis before reaching the age of 3 (Klein, J O (1994) Clin. Inf. Dis 19:823). Left untreated, or becoming chronic, this disease may lead to hearing losses that could be temporary (in the case of fluid accumulation in the middle ear) or permanent (if the auditive nerve is damaged). In infants, such hearing losses may be responsible for a delayed speech learning.

Three bacterial species are primarily isolated from the middle ear of children with otitis media: *Streptococcus pneumoniae*, non typeable *Haemophilus influenzae* (NTHi) and *M. catarrhalis*. They are present in 60 to 90% of the cases. A review of recent studies shows that *S. pneumoniae* and NTHi represent both about 30%, and *M. catarrhalis* about 15% of the otitis media cases (Murphy, T F (1996) Microbiol. Rev. 60:267). Other bacteria could be isolated from the middle ear (*H. influenzae* type B, *S. pyogenes* etc) but at a much lower frequency (2% of the cases or less).

Epidemiological data indicate that, for the pathogens found in the middle ear, the colonization of the upper respiratory tract is an absolute prerequisite for the development of an otitis; other are however also required to lead to the disease (Dickinson, D P et al. (1988) J. Infect. Dis. 158:205, Faden, H L et al. (1991) Ann. Otorhinol. Laryngol. 100:612). These are important to trigger the migration of the bacteria into the middle ear via the Eustachian tubes, followed by the initiation of an inflammatory process. These factors are unknown to date. It has been postulated that a transient anomaly of the immune system following a viral infection, for example, could cause an inability to control the colonization of the respiratory tract (Faden, H L et al (1994) J. Infect. Dis. 169:1312). An alternative explanation is that the exposure to environmental factors allow a more important colonization of some children, who subsequently become susceptible to the development of otitis media because of the sustained presence of middle ear pathogens (Murphy, T F (1996) Microbiol. Rev. 60:267).

The immune response to *M. catarrhalis* is poorly characterized. The analysis of strains isolated sequentially from the nasopharynx of babies followed from 0 to 2 years of age, indicates that they get and eliminate frequently new strains. This indicates that an efficacious immune response against this bacteria is mounted by the colonized children (Faden, H L et al (1994) J. Infect. Dis. 169:1312).

In most adults tested, bactericidal antibodies have been identified (Chapman, A J et al. (1985) J. Infect. Dis. 151:878). Strains of *M. catarrhalis* present variations in their capacity to resist serum bactericidal activity: in general, isolates from diseased individuals are more resistant than those who are simply colonized (Hol, C et al. (1993) Lancet 341:1281, Jordan, K L et al. (1990) Am. J. Med. 88 (suppl. 5A):28S). Serum resistance could therefore be considered as a virulence factor of the bacteria. An opsonizing activity has been observed in the sera of children recovering from otitis media.

The antigens targetted by these different immune responses in humans have not been identified, with the exception of OMP B1, a 84 kDa protein which expression is regulated by iron, and that is recognized by the sera of patients with pneumonia (Sethi, S, et al. (1995) Infect. Immun. 63: 1516), and of UspA1 and UspA2 (Chen D. et al.(1999), Infect. Immun. 67:1310).

A few other membrane proteins present on the surface of *M. catarrhalis* have been characterized using biochemical method, or for their potential implication in the induction of a protective immunity (for review, see Murphy, T F (1996) Microbiol. Rev. 60:267). In a mouse pneumonia model, the presence of antibodies raised against some of them (UspA, CopB) favors a faster clearance of the pulmonary infection. Another polypeptide (OMP CD) is highly conserved among *M. catarrhalis* strains, and presents homologies with a porin of *Pseudomonas aeruginosa*, which has been demonstrated efficacious against this bacterium in animal models.

The frequency of *Moroxella catarrhalis* infections has risen dramatically in the past few decades. This has been attributed to the emergence of multiply antibiotic resistant strains and an increasing population of people with weakened immune systems. It is no longer uncommon to isolate *Moraxella catarrhalis* strains that are resistant to some or all of the standard antibiotics. This phenomenon has created an unmet medical need and demand for new anti-microbial agents, vaccines, drug screening methods, and diagnostic tests for this organism.

SUMMARY OF THE INVENTION

The present invention relates to BASB010, in particular BASB010 polypeptides and BASB010 polynucleotides, recombinant materials and methods for their production. In another aspect, the invention relates to methods for using such polypeptides and polynucleotides, including prevention and treatment of microbial diseases, amongst others. In a further aspect, the invention relates to diagnostic assays for detecting diseases associated with microbial infections and conditions associated with such infections, such as assays for detecting expression or activity of BASB010 polynucleotides or polypeptides.

Various changes and modifications within the spirit and scope of the disclosed invention will become readily apparent to those skilled in the art from reading the following descriptions and from reading the other parts of the present disclosure.

BRIEF DESCRIPTION OF THE DRAWINGS

FIGS. 2A–2D show consecutive segments of sequence alignment for three BASB010-encoding polynucleotides.

FIGS. 3A–3B show consecutive segments of sequence alignment for three BASB010 polypeptides.

DESCRIPTION OF THE INVENTION

Figure 1A:
FIGS. 1A–1L show electrophoresis gels from separate RFLP analyses of strains of BASB010.
Figure 1B:
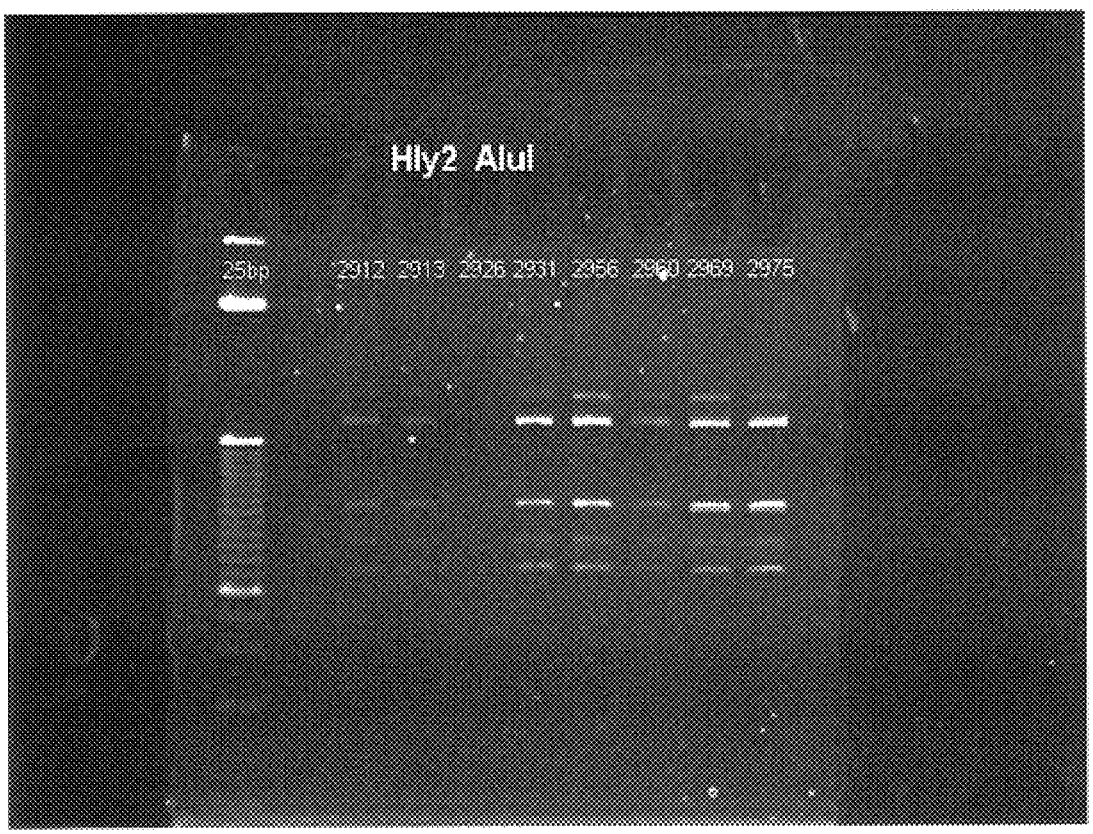
Figure 1C:
Figure 1D:
Figure 1E:
Figure 1F:
Figure 1G:
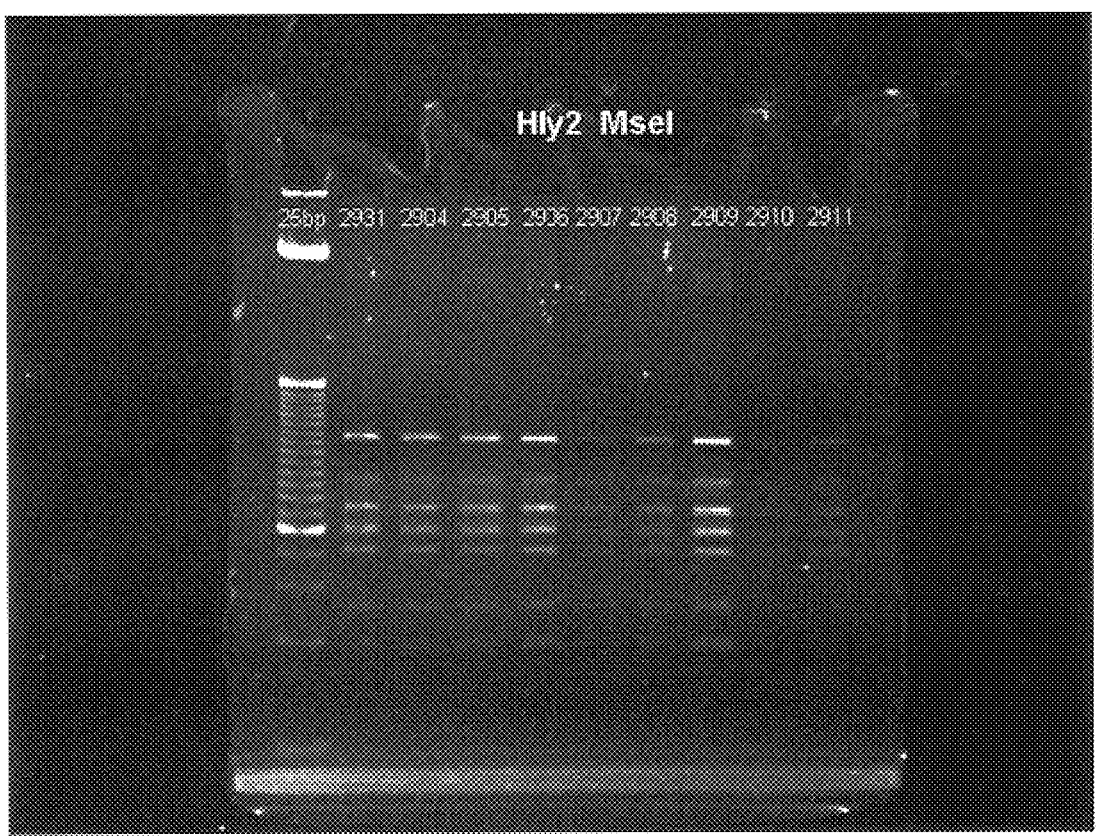
Figure 1H:
Figure 1I:
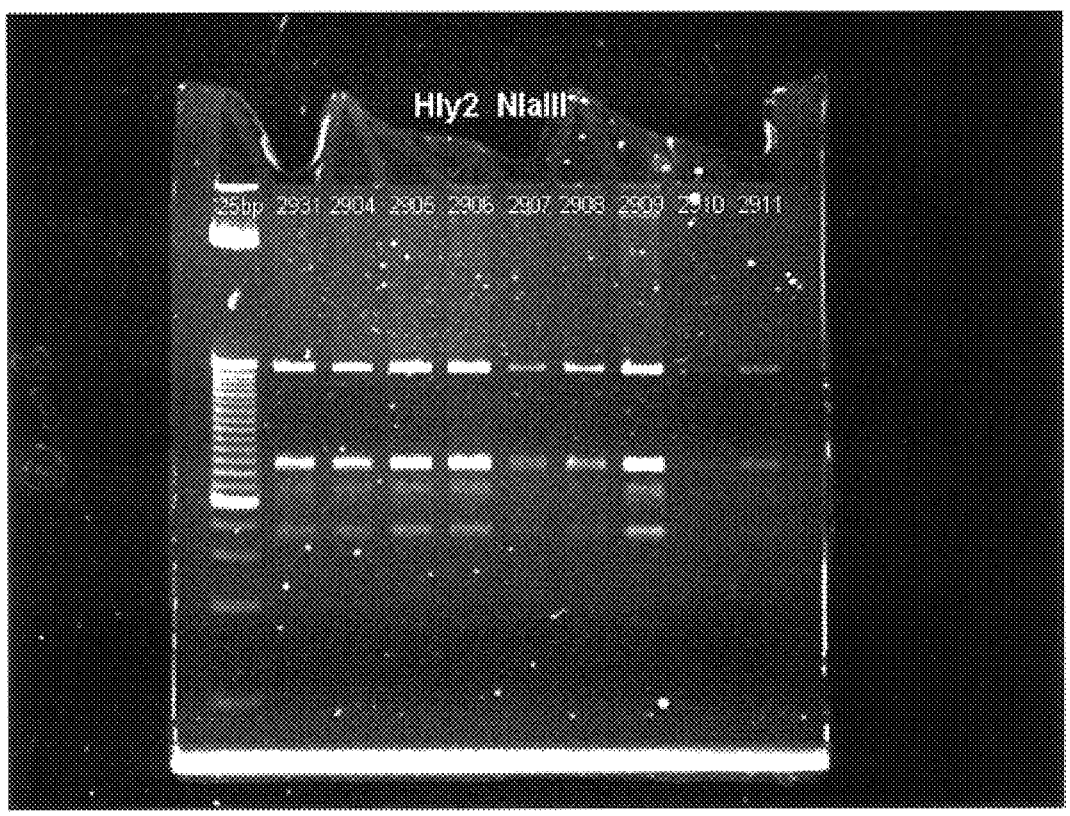
Figure 1J:
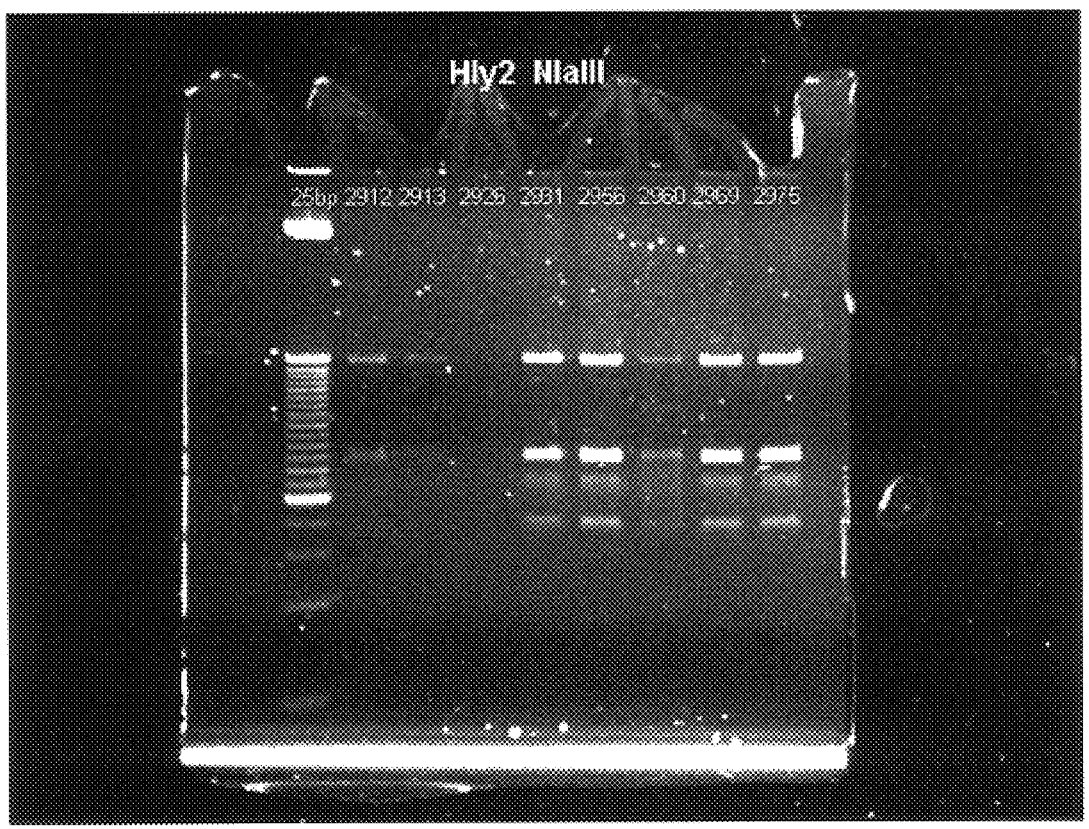
Figure 1K:
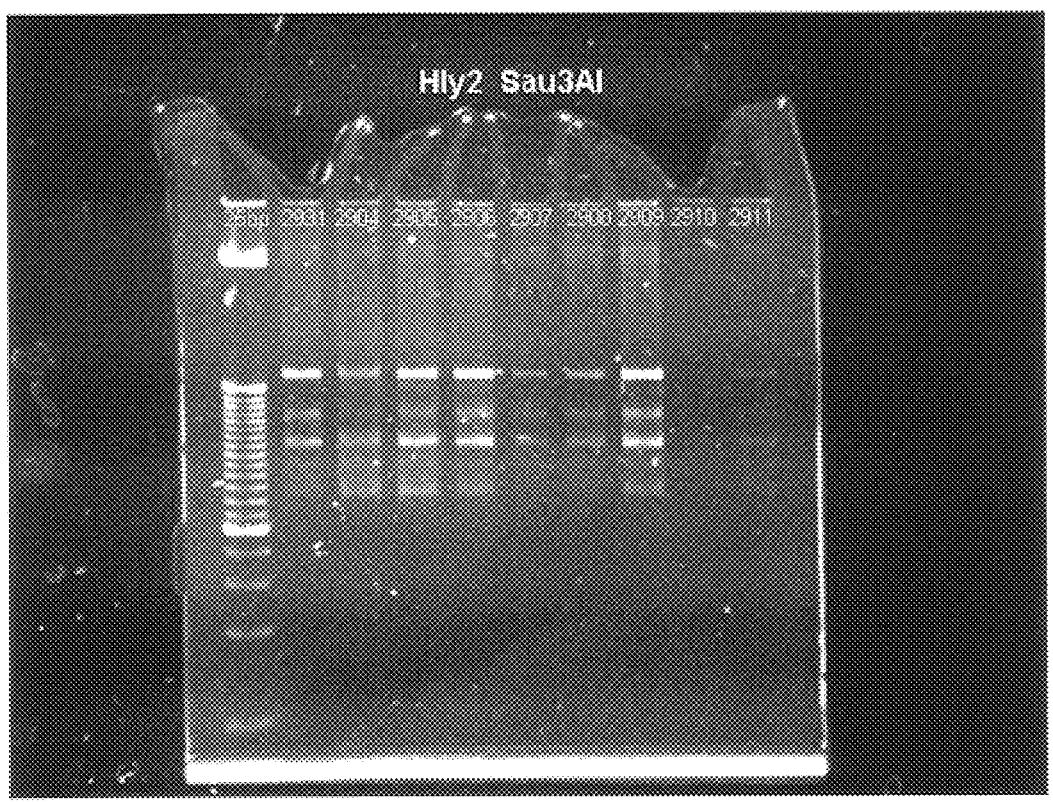
Figure 1L:
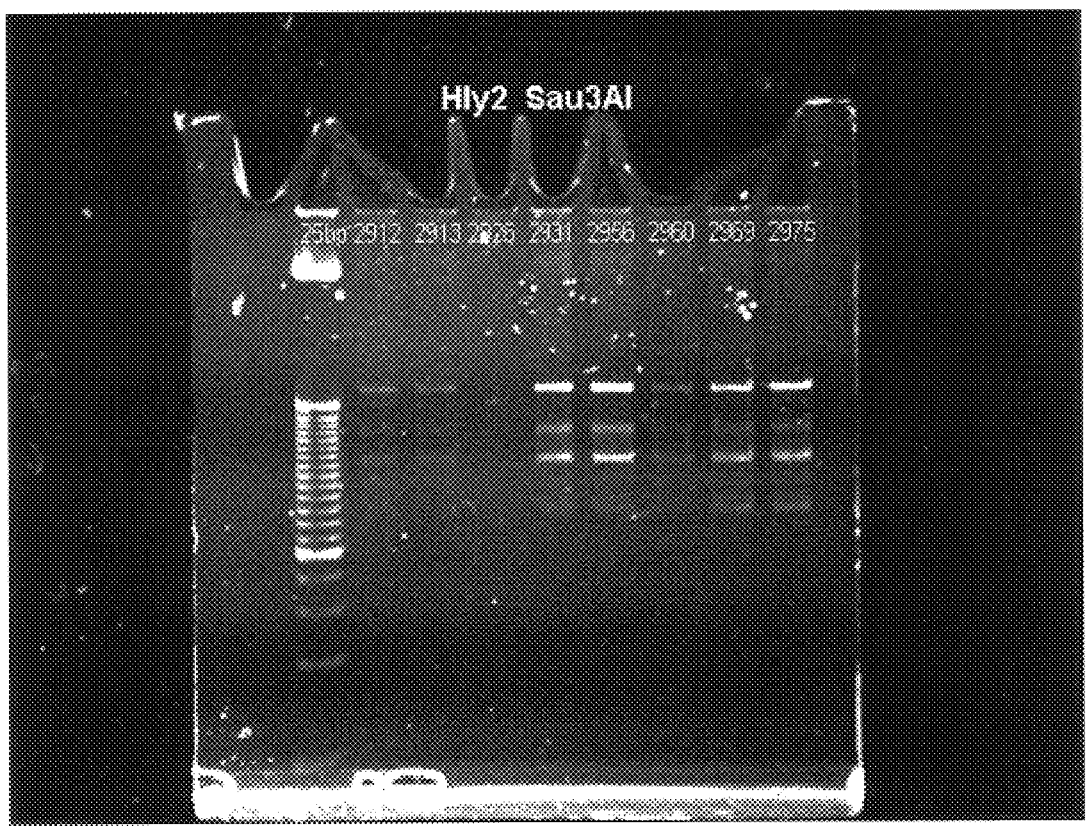

The invention relates to BASB010 polypeptides and polynucleotides as described in greater detail below. In particular, the invention relates to polypeptides and polynucleotides of BASB010 of *Moraxella catarrhalis*, which is related by amino acid sequence homology to TlyC hemolysin protein of *Serpulina hyodysenteriae*. The invention relates especially to BASB010 having the nucleotide and amino acid sequences set out in SEQ ID NO:1, 3 and 5 and SEQ ID NO:2, 4 and 6 respectively. It is understood that sequences recited in the Sequence Listing below as "DNA" represent an exemplification of one embodiment of the invention, since those of ordinary skill will recognize that such sequences can be usefully employed in polynucleotides in general, including ribopolynucleotides.

Polypeptides

In one aspect of the invention there are provided polypeptides of *Moraxella catarrhalis* referred to herein as "BASB010" and "BASB010 polypeptides" as well as biologically, diagnostically, prophylactically, clinically or therapeutically useful variants thereof, and compositions comprising the same.

The present invention further provides for:

(a) an isolated polypeptide which comprises an amino acid sequence which has at least 85% identity, preferably at least 90% identity, more preferably at least 95% identity, most preferably at least 97–99% or exact identity, to that of SEQ ID NO:2, 4 or 6;

(b) a polypeptide encoded by an isolated polynucleotide comprising a polynucleotide sequence which has at least 85% identity, preferably at least 90% identity, more preferably at least 95% identity, even more preferably at least 97–99% or exact identity to SEQ ID NO:1, 3 or 5 over the entire length of SEQ ID NO:1, 3 or 5 respectively; or (c) a polypeptide encoded by an isolated polynucleotide comprising a polynucleotide sequence encoding a polypeptide which has at least 85% identity, preferably at least 90% identity, more preferably at least 95% identity, even more preferably at least 97–99% or exact identity, to the amino acid sequence of SEQ ID NO:2, 4 or 6.

The BASB010 polypeptides provided in SEQ ID NO:2, 4 and 6 are the BASB010 polypeptides from *Moraxella catarrhalis* strains MC2931 (ATCC 43617), MC2911 and MC2969.

The invention also provides an immunogenic fragment of a BASB010 polypeptide, that is, a contiguous portion of the BASB010 polypeptide which has the same or substantially the same immunogenic activity as the polypeptide comprising the amino acid sequence of SEQ ID NO:2, 4 or 6; That is to say, the fragment (if necessary when coupled to a carrier) is capable of raising an immune response which recognises the BASB010 polypeptide. Such an immunogenic fragment may include, for example, the BASB010 polypeptide lacking an N-terminal leader sequence, and/or a transmembrane domain and/or a C-terminal anchor domain.

In a preferred aspect the immunogenic fragment of BASB010 according to the invention comprises substantially all of the extracellular domain of a polypeptide which has at least 85% identity, preferably at least 90% identity, more preferably at least 95% identity, most preferably at least 97–99% identity, to that of SEQ ID NO:2, 4 or 6 over the entire length of SEQ ID NO:2.

A fragment is a polypeptide having an amino acid sequence that is entirely the same as part but not all of any amino acid sequence of any polypeptide of the invention. As with BASB010 polypeptides, fragments may be "freestanding," or comprised within a larger polypeptide of which they form a part or region, most preferably as a single continuous region in a single larger polypeptide.

Preferred fragments include, for example, truncation polypeptides having a portion of an amino acid sequence of SEQ ID NO:2, 4 or 6 or of variants thereof, such as a continuous series of residues that includes an amino- and/or carboxyl-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2, 4 or 6, or an isolated polypeptide comprising an amino acid sequence having at least 15, 20, 30, 40, 50 or 100 contiguous amino acids truncated or deleted from the amino acid sequence of SEQ ID NO:2, 4 or 6.

Particularly preferred are variants in which several, 5–10, 1–5, 1–3, 1–2 or 1 amino acids are substituted, deleted, or added in any combination.

Fragments of the polypeptides of the invention may be employed for producing the corresponding full-length polypeptide by peptide synthesis; therefore, these variants may be employed as intermediates for producing the full-length polypeptides of the invention.

The polypeptides, or immunogenic fragments, of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa.

Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenzae* and the non-structural protein from influenza virus, NS1 (hemagglutinin). Another fusion partner is the protein known as LYTA. Preferably the C terminal portion of the molecule is used. Lyta is derived from *Streptococcus pneumoniae* which synthesize an N-acetyl-L-alanine amidase, LytA, (coded by the lytA gene {Gene, 43 (1986) page 265–272}) an autolysin that specifically degrades certain bonds in the peptidoglycan backbone. The C-terminal domain of the LytA protein is responsible for the affinity to the choline or to some choline analogues such as DEAE. This property has been exploited for the development of *E. coli* C-LytA expressing plasmids useful for expression of fusion proteins. Purification of hybrid proteins containing the C-LytA fragment at its amino terminus has been described {Biotechnology: 10, (1992) page 795–798}. It is possible to use the repeat portion of the LytA molecule found in the C terminal end starting at residue 178, for example residues 188–305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

It is most preferred that a polypeptide of the invention is derived from *Moraxella catarrhalis*, however, it may preferably be obtained from other organisms of the same taxonomic genus. A polypeptide of the invention may also be obtained, for example, from organisms of the same taxonomic family or order.

Polynucleotides

It is an object of the invention to provide polynucleotides that encode BASB010 polypeptides, particularly polynucleotides that encode the polypeptide herein designated BASB010.

In a particularly preferred embodiment of the invention the polynucleotide comprises a region encoding BASB010 polypeptides comprising a sequence set out in SEQ ID NO:1, 3 or 5 which includes a full length gene, or a variant thereof.

The BASB010 polynucleotides provided in SEQ ID NO:1, 3 and 5 are the BASB010 polynucleotides from *Moraxella catarrhalis* strains MC2931 (ATCC 43617), MC2911 and MC2969.

As a further aspect of the invention there are provided isolated nucleic acid molecules encoding and/or expressing BASB010 polypeptides and polynucleotides, particularly *Moraxella catarrhalis* BASB010 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB010 polypeptide having a deduced amino acid sequence of SEQ ID NO:2, 4 or 6 and polynucleotides closely related thereto and variants thereof.

In another particularly preferred embodiment of the invention there is a BASB010 polypeptide from *Moraxella catarrhalis* comprising or consisting of an amino acid sequence of SEQ ID NO:2, 4 or 6 or a variant thereof.

Using the information provided herein, such as a polynucleotide sequence set out in SEQ ID NO:1, 3 or 5, a polynucleotide of the invention encoding BASB010 polypeptide may be obtained using standard cloning and screening methods, such as those for cloning and sequencing chromosomal DNA fragments from bacteria using *Moraxella catarrhalis* Catlin cells as starting material, followed by obtaining a full length clone. For example, to obtain a polynucleotide sequence of the invention, such as a polynucleotide sequence given in SEQ ID NO:1, 3 or 5, typically a library of clones of chromosomal DNA of *Moraxella catarrhalis* Catlin in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, New York (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:1, 3 or 5 was discovered in a DNA library derived from *Moraxella catarrhalis*.

Moreover, each DNA sequence set out in SEQ ID NO:1, 3 or 5 contains an open reading frame encoding a protein having about the number of amino acid residues set forth in SEQ ID NO:2, 4 or 6 with a deduced molecular weight that can be calculated using amino acid residue molecular weight values well known to those skilled in the art.

The polynucleotide of SEQ ID NO:1, between the start codon at nucleotide number 1 and the stop codon which begins at nucleotide number 1174 of SEQ ID NO:1, encodes the polypeptide of SEQ ID NO:2.

The polynucleotide of SEQ ID NO:3, between the start codon at nucleotide number 1 and the stop codon which begins at nucleotide number 1174 of SEQ ID NO:3, encodes the polypeptide of SEQ ID NO:4.

The polynucleotide of SEQ ID NO:5, between the start codon at nucleotide number 1 and the stop codon which begins at nucleotide number 1174 of SEQ ID NO:5, encodes the polypeptide of SEQ ID NO:6.

In a further aspect, the present invention provides for an isolated polynucleotide comprising or consisting of:

(a) a polynucleotide sequence which has at least 85% identity, preferably at least 90% identity, more preferably at least 95% identity, even more preferably at least 97–99% or exact identity to SEQ ID NO:1, 3 or 5 over the entire length of SEQ ID NO:1, 3 or 5 respectively; or (b) a polynucleotide sequence encoding a polypeptide which has at least 85% identity, preferably at least 90% identity, more preferably at least 95% identity, even more preferably at least 97–99% or 100% exact, to the amino acid sequence of SEQ ID NO:2, 4 or 6, over the entire length of SEQ ID NO:2, 4 or 6 respectively.

A polynucleotide encoding a polypeptide of the present invention, including homologs and orthologs from species other than *Moraxella catarrhalis*, may be obtained by a process which comprises the steps of screening an appropriate library under stringent hybridization conditions (for example, using a temperature in the range of 45–65° C. and an SDS concentration from 0.1–1%) with a labeled or detectable probe consisting of or comprising the sequence of SEQ ID NO:1, 3 or 5 or a fragment thereof; and isolating a full-length gene and/or genomic clones containing said polynucleotide sequence.

The invention provides a polynucleotide sequence identical over its entire length to a coding sequence (open reading frame) in SEQ ID NO:1, 3 or 5. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or preproprotein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB010 polypeptide of SEQ ID NO:2, 4 or 6 may be identical to the polypeptide encoding sequence contained in nucleotides 1 to 1173 of SEQ ID NO:1, 3 or 5. Alternatively it may be a sequence, which as a result of the redundancy (degeneracy) of the genetic code, also encodes the polypeptide of SEQ ID NO:2, 4 or 6.

The term "polynucleotide encoding a polypeptide" as used herein encompasses polynucleotides that include a sequence encoding a polypeptide of the invention, particularly a bacterial polypeptide and more particularly a polypeptide of the *Moraxella catarrhalis* BASB010 having an amino acid sequence set out in SEQ ID NO:2, 4 or 6. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:2, 4 or 6. Fragments of polynucleotides of the invention may be used, for example, to synthesize full-length polynucleotides of the invention.

Further particularly preferred embodiments are polynucleotides encoding BASB010 variants, that have the amino acid sequence of BASB010 polypeptide of SEQ ID NO:2, 4 or 6 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB010 polypeptide.

Further preferred embodiments of the invention are polynucleotides that are at least 85% identical over their entire length to a polynucleotide encoding BASB010 polypeptide having an amino acid sequence set out in SEQ ID NO:2, 4 or 6, and polynucleotides that are complementary to such polynucleotides. Alternatively, most highly preferred are polynucleotides that comprise a region that is at least 90% identical over its entire length to a polynucleotide encoding BASB010 polypeptide and polynucleotides complementary thereto. In this regard, polynucleotides at least 95% identical over their entire length to the same are particularly preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:1, 3 or 5.

In accordance with certain preferred embodiments of this invention there are provided polynucleotides that hybridize, particularly under stringent conditions, to BASB010 polynucleotide sequences, such as those polynucleotides in SEQ ID NO:1, 3 or 5.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:1, 3 or 5 under stringent hybridization conditions with a probe having the sequence of said polynucleotide sequence set forth in SEQ ID NO:1, 3 or 5 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB010 and to isolate cDNA and genomic clones of other genes that have a high identity, particularly high sequence identity, to the BASB010 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB010 gene may be isolated by screening using a DNA sequence provided in SEQ ID NO:1, 3 or 5 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NOS:-1, 3 and 5 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolff et al., *Hum Mol Genet* (1992) 1: 363, Manthorpe et al., *Hum. Gene Ther.* (1983) 4: 419), delivery of DNA complexed with specific protein carriers (Wu et al., *J Biol Chem.* (1989) 264: 16985), coprecipitation of DNA with calcium phosphate (Benvenisty & Reshef, *PNAS USA*, (1986) 83: 9551), encapsulation of DNA in various forms of liposomes (Kaneda et al., *Science* (1989) 243: 375), particle bombardment (Tang et al., *Nature* (1992) 356:152, Eisenbraun et al., *DNA Cell Biol* (1993) 12: 791) and in vivo infection using cloned retroviral vectors (Seeger et al., *PNAS USA* (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al, *BASIC METHODS IN MOLECULAR BIOLOGY*, (1986) and Sambrook, et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci, *E. coli*, streptomyces, cyanobacteria, *Bacillus subtilis, Neisseria meningitidis*, and *Moraxella catarrhalis*; fungal cells, such as cells of a yeast, Kluveromyces, Saccharomyces, a basidiomycete, *Candida albicans* and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g; vaccinia, fowlpox, canarypox), alphaviruses (Sindbis virus, Semliki Forest Virus, Venezuelian Equine Encephalitis Virus), adenoviruses, adeno-associated virus, picornaviruses (poliovirus, rhinovirus), herpesviruses (varicella zoster virus, etc), Listeria, Salmonella, Shigella Neisseria, BCG. These viruses and bacteria can be virulent, or attenuated in various ways in order to obtain live vaccines. Such live vaccines also form part of the invention.

Diagnostic, Prognostic, Serotyping and Mutation Assays

This invention is also related to the use of BASB010 polynucleotides and polypeptides of the invention for use as diagnostic reagents. Detection of BASB010 polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the BASB010 gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled BASB010 polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science*, 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad. Sci., USA*, 85: 4397–4401 (1985).

In another embodiment, an array of oligonucleotides probes comprising BASB010 nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., *Science*, 274: 610 (1996)).

Thus in another aspect, the present invention relates to a diagnostic kit which comprises:

(a) a polynucleotide of the present invention, preferably the nucleotide sequence of SEQ ID NO:1, 3 or 5, or a fragment thereof;

(b) a nucleotide sequence complementary to that of (a);

(c) a polypeptide of the present invention, preferably the polypeptide of SEQ ID NO:2, 4 or 6 or a fragment thereof; or (d) an antibody to a polypeptide of the present invention, preferably to the polypeptide of SEQ ID NO:2, 4 or 6.

It will be appreciated that in any such kit, (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferable, SEQ ID NO:1, 3 or 5, which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding BASB010 polypeptide can be used to identify and analyze mutations.

The invention further provides primers with 1, 2, 3 or 4 nucleotides removed from the 5' and/or the 3' end. These primers may be used for, among other things, amplifying BASB010 DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferably bacterial infections, more preferably infections caused by *Moraxella catarrhalis*, comprising determining from a sample derived from an individual, such as a bodily material, an increased level of expression of polynucleotide having a sequence of SEQ ID NO:1, 3 or 5. Increased or decreased expression of a BASB010 polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of BASB010 polypeptide compared to normal control tissue samples may be used to detect the presence of an infection, for example. Assay techniques that can be used to determine levels of a BASB010 polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probes obtained or derived from a bodily sample, to determine the presence of a particular polynucleotide sequence or related sequence in an individual. Such a presence may indicate the presence of a pathogen, particularly *Moraxella catarrhalis*, and may be useful in diagnosing and/or prognosing disease or a course of disease. A grid comprising a number of variants of the polynucleotide sequence of SEQ ID NO:1, 3 or 5 are preferred. Also preferred is a comprising a number of variants of a polynucleotide sequence encoding the polypeptide sequence of SEQ ID NO:2, 4 or 6.

Antibodies

The polypeptides and polynucleotides of the invention or variants thereof, or cells expressing the same can be used as immunogens to produce antibodies immunospecific for such polypeptides or polynucleotides respectively.

In certain preferred embodiments of the invention there are provided antibodies against BASB010 polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495–497 (1975); Kozbor et al., Immunology Today 4: 72 (1983); Cole et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms or animals, such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-BASB010 or from naive libraries (McCafferty, et al., (1990), Nature 348, 552–554; Marks, et al., (1992) Biotechnology 10, 779–783). The affinity of these antibodies can also be improved by, for example, chain shuffling (Clackson et al., (1991) Nature 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against BASB010 polypeptide or BASB010 polynucleotide may be employed to treat infections, particularly bacterial infections.

Polypeptide variants include antigenically, epitopically or immunologically equivalent variants form a particular aspect of this invention.

Preferably, the antibody or variant thereof is modified to make it less immunogenic in the individual. For example, if the individual is human the antibody may most preferably be "humanized," where the complimentarity determining region or regions of the hybridoma-derived antibody has been transplanted into a human monoclonal antibody, for example as described in Jones et al. (1986), Nature 321, 522–525 or Tempest et al., (1991) Biotechnology 9, 266–273.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2): Chapter 5 (1991).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring BASB010 polypeptide and/or polynucleotide activity in the mixture, and comparing the BASB010 polypeptide and/or polynucleotide activity of the mixture to a standard. Fusion proteins, such as those made from Fc portion and BASB010 polypeptide, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52–58 (1995); and K. Johanson et al., J Biol Chem, 270(16): 9459–9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of BASB010 polypeptides or polynucleotides, particularly those compounds that are bacteriostatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising BASB010 polypeptide and a labeled substrate or ligand of such polypeptide is incubated in the absence or the presence of a candidate molecule that may be a BASB010 agonist or antagonist. The ability of the candidate molecule to agonize or antagonize the BASB010 polypeptide is reflected in decreased binding of the labeled ligand or decreased production of product from such substrate. Molecules that bind gratuitously, i.e., without inducing the effects of BASB010 polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to calorimetric, labeled substrate converted into product, a reporter gene that is responsive to changes in BASB010 polynucleotide or polypeptide activity, and binding assays known in the art.

Another example of an assay for BASB010 agonists is a competitive assay that combines BASB010 and a potential agonist with BASB010-binding molecules, recombinant BASB010 binding molecules, natural substrates or ligands, or substrate or ligand mimetics, under appropriate conditions for a competitive inhibition assay. BASB010 can be labeled, such as by radioactivity or a calorimetric compound, such that the number of BASB010 molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing BASB010-induced activities, thereby preventing the action or expression of BASB010 polypeptides and/or polynucleotides by excluding BASB010 polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLE-OTIDES AS ANTISENSE INHIBITORS OF GENE EXPRESSION*, CRC Press, Boca Raton, Fla. (1988), for a description of these molecules). Preferred potential antagonists include compounds related to and variants of BASB010.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial BASB010 proteins that mediate tissue damage and/or; to block the normal progression of pathogenesis in infections initiated other than by the implantation of in-dwelling devices or by other surgical techniques.

In accordance with yet another aspect of the invention, there are provided BASB010 agonists and antagonists, preferably bacteristatic or bactericidal agonists and antagonists.

The antagonists and agonists of the invention may be employed, for instance, to prevent, inhibit and/or treat diseases.

In a further aspect, the present invention relates to mimotopes of the polypeptide of the invention. A mimotope is a peptide sequence, sufficiently similar to the native peptide (sequentially or structurally), which is capable of being recognised by antibodies which recognise the native peptide; or is capable of raising antibodies which recognise the native peptide when coupled to a suitable carrier.

Peptide mimotopes may be designed for a particular purpose by addition, deletion or substitution of elected amino acids. Thus, the peptides may be modified for the purposes of ease of conjugation to a protein carrier. For example, it may be desirable for some chemical conjugation methods to include a terminal cysteine. In addition it may be desirable for peptides conjugated to a protein carrier to include a hydrophobic terminus distal from the conjugated terminus of the peptide, such that the free unconjugated end of the peptide remains associated with the surface of the carrier protein. Thereby presenting the peptide in a conformation which most closely resembles that of the peptide as found in the context of the whole native molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide.

Alternatively, peptide mimotopes may be identified using antibodies which are capable themselves of binding to the polypeptides of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native polypeptide.

Vaccines

Another aspect of the invention relates to a method for inducing an immunological response in an individual, particularly a mammal, preferably humans, which comprises inoculating the individual with BASB010 polynucleotide and/or polypeptide, or a fragment or variant thereof, adequate to produce antibody and/or T cell immune response to protect said individual from infection, particularly bacterial infection and most particularly *Moraxella catarrhalis* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of BASB010 polynucleotide and/or polypeptide, or a fragment or a variant thereof, for expressing BASB010 polynucleotide and/or polypeptide, or a fragment or a variant thereof in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a BASB010 polynucleotide and/or polypeptide encoded therefrom, wherein the composition comprises a recombinant BASB010 polynucleotide and/or polypeptide encoded therefrom and/or comprises DNA and/or RNA which encodes and expresses an antigen of said BASB010 polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+ T cells.

A BASB010 polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from *Haemophilus influenzae*, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

Provided by this invention are compositions, particularly vaccine compositions, and methods comprising the polypeptides and/or polynucleotides of the invention and immunostimulatory DNA sequences, such as those described in Sato, Y. et al. *Science* 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with *Moraxella catarrhalis*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Moraxella catarrhalis* infection, in mammals, particularly humans.

The invention also includes a vaccine formulation which comprises an immunogenic recombinant polypeptide and/or polynucleotide of the invention together with a suitable carrier, such as a pharmaceutically acceptable carrier. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteristatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4+ve T cell clones by Mosmann and Coffman (Mosmann, T. R. and Coffman, R. L. (1989) TH1 and TH2 cells: different patterns of lymphokine secretion lead to different functional properties. *Annual Review of Immunology*, 7, p145–173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2-type responses are associated with the secretion of IL4, IL-5, IL-6 and IL-13.

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+ cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (European Patent number 0 689 454). 3D-MPL will be present in the range of 10 μg–100 μg preferably 25–50 μg per dose wherein the antigen will typically be present in a range 2–50 μg per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with an carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 1:1; preferably 1:5 to 5:1 and often substantially 1:1. The preferred range for optimal synergy is 2.5:1 to 1:1 3D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 μg–200 μg, such as 10–100 μg, preferably 10 μg–50 μg per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, autoimmune diseases and related conditions. Such a polyvalent vaccine composition may include a TH-1 inducing adjuvant as hereinbefore described.

While the invention has been described with reference to certain BASB010 polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

Compositions, Kits and Administration

In a further aspect of the invention there are provided compositions comprising a BASB010 polynucleotide and/or a BASB010 polypeptide for administration to a cell or to a multicellular organism.

The invention also relates to compositions comprising a polynucleotide and/or a polypeptides discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention.

Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, solutions, powders and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgment of the attending practitioner. Suitable dosages, however, are in the range of 0.1–100 μg/kg of subject.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as the GCG program package.

Also provided by the invention are methods for the analysis of character sequences or strings, particularly genetic sequences or encoded protein sequences. Preferred methods of sequence analysis include, for example, methods of sequence homology analysis, such as identity and similarity analysis, DNA, RNA and protein structure analysis, sequence assembly, cladistic analysis, sequence motif analysis, open reading frame determination, nucleic acid base calling, codon usage analysis, nucleic acid base trimming, and sequencing chromatogram peak analysis.

A computer based method is provided for performing homology identification. This method comprises the steps of: providing a first polynucleotide sequence comprising the sequence of a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

DEFINITIONS

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heine, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., *Nucleic Acids Research* 12(1): 387 (1984)), BLASTP, BLASTN (Altschul, S. F. et al., *J. Molec. Biol.* 215: 403–410 (1990), and FASTA( Pearson and Lipman Proc. Natl. Acad. Sci. USA 85; 2444–2448 (1988). The BLAST family of programs is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following:

Algorithm: Needleman and Wunsch, J. Mol Biol. 48: 443–453 (1970)

Comparison matrix: BLOSSUM62 from Henikoff and Henikoff,

Proc. Natl. Acad. Sci. USA. 89:10915–10919 (1992)

Gap Penalty: 8

Gap Length Penalty: 2

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \cdot y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Individual(s)," when used herein with reference to an organism, means a multicellular eukaryote, including, but not limited to a metazoan, a mammal, an ovid, a bovid, a simian, a primate, and a human.

"Isolated" means altered "by the hand of man" from its natural state, ie., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxyribonucleotide, which may be unmodified RNA or DNA or modified RNA or DNA including single and double-stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Disease(s)" means any disease caused by or related to infection by a bacteria, including, for example, otitis media in infants and children, pneumonia in elderlies, sinusitis, nosocomial infections and invasive diseases, chronic otitis media with hearing loss, fluid accumulation in the middle ear, auditive nerve damage, delayed speech learning, infection of the upper respiratory tract and inflammation of the middle ear.

EXAMPLES

The examples below are carried out using standard techniques, which are well known and routine to those of skill in the art, except where otherwise described in detail. The examples are illustrative, but do not limit the invention.

Example 1

Discovery and confirmatory DNA sequencing of the BASB010 gene from *Moraxella catarrhalis* strain ATCC 43617.

The BASB010 gene of SEQ ID NO:1 was first discovered in the Incyte PathoSeq data base containing unfinished genomic DNA sequences of the *Moraxella catarrhalis* strain ATCC 43617 (also referred to as strain Mc2931). The translation of the BASB010 polynucleotide sequence, shown in SEQ ID NO:2, showed significant similarity (31% identity in a 157 amino acids overlap) to the TlyC hemolysin protein of *Serpulina hyodysenteriae*. It should be noted that the start codon of the BASB010 gene is TTG, which is not usual among bacterial genes. The TTG codon has been translated as methionine.

The sequence of the BASB010 gene was further confirmed experimentally. For this purpose, genomic DNA was extracted from $10^{10}$ cells of the *M. catarrhalis* cells (strain ATCC 43617) using the QIAGEN genomic DNA extraction kit (Qiagen Gmbh), and 1 µg of this material was submitted to Polymerase Chain Reaction DNA amplification using primers E475779 (5'-CCA AAA TGT GGC AAA TTT GTC-3') [SEQ ID NO:7] and E475780 (5'-CTT AAA ACA GAA CGG GTG CTG-3') [SEQ ID NO:8]. This PCR product was purified on a Biorobot 9600 (Qiagen Gmbh) apparatus and subjected to DNA sequencing using the Big Dye Cycle Sequencing kit (Perkin-Elmer) and an ABI 377/PRISM DNA sequencer. DNA sequencing was performed on both strands with a redundancy of 2 and the full-length sequence was assembled using the Sequencher™ software (Applied Biosytems). The resulting DNA sequence turned out to be 100% identical to SEQ ID NO:1.

Example 2

Variability Analysis of the BASB010 Gene Among Several *Moraxella catarrhalis* Strains 2A: Restriction Fragment Length Analysis (RFLP).

Genomic DNA was extracted from 16 *M. catarrhalis* strains (presented in Table 1) as described below. *M. catarrhalis* was streaked for single colonies on BHI agar plates and grown overnight at 37° C. Three or four single colonies were picked and used to inoculate a ~1.5 ml BHI (Brain-heart infusion) broth seed culture which was grown overnight in a shaking incubator, ~300 rpm, at 37° C. A 500 ml erlenmeyer flask containing ~150 ml of BHI broth was inoculated with the seed culture and grown for ~12–16 hours at 37° C. in a shaking incubator, ~175 rpm, to generate cell mass for DNA isolation. Cells were collected by centrifugation in a Sorvall GSA rotor at ~2000×g for 15 minutes at room temperature. The supernatant was removed and the cell pellet suspended in ~5.0 ml of sterile water. An equal volume of lysis buffer (200 mM NaCl, 20 mM EDTA, 40 mM Tris-Hcl, pH 8.0, 0.5% (w/v) SDS, 0.5% (v/v) 2-mercaptoethanol, and 250 µg/ml of proteinase K) was added and the cells suspended by gentle agitation and trituration. The cell suspension was then incubated ~12 hours at 50° C. to lyse the bacteria and liberate chromosomal DNA. Proteinaceous material was precipitated by the addition of 5.0 ml of saturated NaCl (~6.0 M, in sterile water) and centrifugation at ~5,500 g in a Sorvall SS34 rotor at room temperature. Chromosomal DNA was precipitated from the cleared supernatant by the addition of two volumes of 100% ethanol. Aggregated DNA was collected and washed using gentle agitation in a small volume of a 70% ethanol solution. Purified chromosomal DNA was suspended in sterile water and allowed to dissolve/disburse overnight at 4° C. by gentle rocking. The concentration of dissolved DNA was determined spectrophotometrically at 260 nm using an extinction coefficient of 1.0 O.D. unit ~50 µg/ml.

This material was next submitted to PCR amplification using the MC-Hem2-Nco-gIIIF (5'-ATC CAG AGG GCC ATG GCG TTT GAG CTT GGT GGC ACA CCG AC-3') [SEQ ID NO:9] and MC-Hem2-Xba-gIIIRC (5'-ATC CAG AGG TTC TAG ACC CTT TTC ATC AAA CGG TGC ATC TTC-3') [SEQ ID NO:10] oligonucleotides. The corresponding BASB010 gene amplicons were then subjected independently to hydrolysis using restriction enzymes (AluI, HindII, HphI, NlaIII, MseI, Sau3AI,) and restriction products were separated by agarose or polyacrylamide gel electrophoresis using standard molecular biology procedures as described in "Molecular Cloning, a Laboratory Manual, Second Edition, Eds: Sambrook, Fritsch & Maniatis, Cold Spring Harbor press 1989". The photographs of the resulting electrophoresis gels are displayed in FIG. 1. For each strain, RFLP patterns corresponding to the 6 restriction enzymes were scored and combined. Groups of strains sharing identical combination of RFLP patterns were then defined. Using this methodology, the strains tested in this study fell into a single genomic group (Group 1: Mc2904, Mc2911, Mc2912, Mc2956 and Mc2969, Mc2905, Mc2906, Mc2907, Mc2908, Mc2910, Mc2913, Mc2926, Mc2975, Mc2909, Mc2931, Mc2960). These data support that the *Moraxella catarrhalis* population used in this study displays limited nucleotide sequence diversity for the BASB010 gene.

2B: DNA Sequencing in Other Strains.

Using the experimental procedure as described in example 1, the sequence of the BASB010 gene was also determined for other *Moraxella catarrhalis* strains (Mc2911 and Mc2969). The polynucleotide sequences of the BASB010 gene of the strains Mc2911 and Mc2969 are shown in SEQ ID NO:3 and 5, respectively. These polynucleotide sequences were translated into amino acid sequences, which are shown in SEQ ID NO:4 and 6, respectively. Using the MegAlign program from the DNASTAR Lasergene package, a multiple alignment of the polynucleotide sequences of SEQ ID NO:1, 3 and 5 was performed, and is displayed in FIG. 2. A pairwise comparison of identities is summarized in Table 2, showing that the four BASB010 nucleotide gene sequences are all similar at identity level greater than 99%. Using the same program, a multiple alignment of the polypeptide sequences of SEQ ID NO:2, 4 and 6 was performed, and is displayed in FIG. 3. A pairwise comparison of identities is summarized in Table 3, showing that the five BASB010 protein sequences are all similar at a identity level greater than 99%.

TABLE 1

Features of the *Moraxella catarrhalis* strains used in this study

| Strain | Isolated in: | from: |
| --- | --- | --- |
| Mc2904 | USA | Tympanocentesis |
| Mc2905 | USA | Tympanocentesis |
| Mc2906 | USA | Tympanocentesis |
| Mc2907 | USA | Tympanocentesis |
| Mc2908 | USA | Acute otitis Tympanocentesis |
| Mc2909 | USA | Tympanocentesis |
| Mc2910 | USA | Tympanocentesis |
| Mc2911 | USA | Acute otitis Tympanocentesis |
| Mc2912 | USA | Acute otitis Tympanocentesis |
| Mc2913 | USA | Acute otitis Tympanocentesis |
| Mc2926 | USA | ATCC49143 |
| Mc2931 /ATCC | USA | Transtracheal aspirate |
| Mc2956 | Finland | Middle ear fluid |
| Mc2960 | Finland | Middle ear fluid |
| Mc2969 | Norway | Nasopharynx (Pharyngitis-Rhinitis) |
| Mc2975 | Norway | Nasopharynx (Rhinitis) |

TABLE 2

Pairwise identities of the BASB010 polypeptide sequences (in %)

|  | Seq ID No:3 | Seq ID No.5 |
| --- | --- | --- |
| Seq ID No:1 | 99.7 | 100. |
| Seq ID No:3 |  | 99.7 |

TABLE 3

Pairwise identities of the BASB010 polypeptide sequences (in %)

|  | Seq ID No:4 | Seq ID No:6 |
| --- | --- | --- |
| Seq ID No:2 | 99.2 | 100. |
| Seq ID No:4 |  | 99.2 |

Example 3

Construction of Plasmid to Express Recombinant BASB010

A: Cloning of BASB010.

The NcoII and XbaI restriction sites engineered into the forward ([SEQ ID NO:9]) and reverse ([SEQ ID NO:10]) amplification primers, respectively, permitted directional cloning of the BASB010 PCR product into the commercially available *E. coli* expression plasmid pBADgIII (anvitrogen, ampicillin resistant) such that a mature BASB010 protein could be expressed as a fusion protein containing a (His)6 affinity chromatography tag at the C-terminus. The BASB010 PCR product was purified from the amplification reaction using silica gel-based spin columns (QiaGen) according to the manufacturers instructions. To produce the required NcoI and XbaI termini necessary for cloning, purified PCR product was sequentially digested to completion with NcoI and XbaI restriction enzymes as recommended by the manufacturer (Life Technologies). Following the first restriction digestion, the PCR product was purified via spin column as above to remove salts and eluted in sterile water prior to the second enzyme digestion. The digested DNA fragment was again purified using silica gel-based spin columns prior to ligation with the pBADgIII plasmid.

B: Production of Expression Vector.

To prepare the expression plasmid pBADgIII for ligation, it was similarly digested to completion with both NcoI and XbaI and then treated with calf intestinal phosphatase (CIP, ~0.02 units/pmole of 5' end, Life Technologies) as directed by the manufacturer to prevent self ligation. An approximately 5-fold molar excess of the digested fragment to the prepared vector was used to program the ligation reaction. A standard ~20 µl ligation reaction (~16° C., ~16 hours), using methods well known in the art, was performed using T4 DNA ligase (~2.0 units/reaction, Life Technologies). An aliquot of the ligation (~5 µl) was used to transform electrocompetent M15(pREP4) cells according to methods well known in the art. Following a ~2–3 hour outgrowth period at 37° C. in ~1.0 ml of LB broth, transformed cells were plated on LB agar plates containing ampicillin (100 µg/ml) and were incubated overnight at 37° C. Recombinants were identified by whole cell-based PCR analysis.

C: Expression Analysis of PCR-Positive Transformants.

For each PCR-positive transformant identified above, ~5.0 ml of LB broth containing ampicillin (100 µg/ml) was inoculated with cells from the patch plate and grown overnight at 37° C. with shaking (~250 rpm). An aliquot of the overnight seed culture (~1.0 ml) was inoculated into a 125 ml erlenmeyer flask containing ~25 of LB Kn/Ap broth and grown at 37° C. with shaking (~250 rpm) until the culture turbidity reached O.D. 600 of ~0.5, i.e. mid-log phase (usually about 1.5–2.0 hours). At this time approximately half of the culture (~12.5 ml) was transferred to a second 125 ml flask and expression of recombinant BASB010 protein induced by the addition of arabinose to a final concentration of 2% (2 g/100 ml). Incubation of both the induced and non-induced cultures continued for an additional ~4 hours at 37° C. with shaking. Samples (~1.0 ml) of both induced and non-induced cultures were removed after the induction period and the cells collected by centrifugation in a microcentrifuge at room temperature for ~3 minutes. Individual cell pellets were suspended in ~50 µl of sterile water, then mixed with an equal volume of 2×Laemelli SDS-PAGE sample buffer containing 2-mercaptoethanol, and placed in boiling water bath, for ~3 min to denature protein. Equal volumes (~15 µl) of both the crude induced and the non-induced cell lysates were loaded onto duplicate 12% Tris/glycine polyacrylamide gel (1 mm thick Mini-gels, Novex). The induced and non-induced lysate samples were electrophoresed together with prestained molecular weight markers (SeeBlue, Novex) under conventional conditions using a standard SDS/Tris/glycine running buffer (BioRad). Following electrophoresis, one gel was stained with commassie brilliant blue R250 (BioRad) and then destained to visualize novel BASB010 IPTG-inducible protein(s). The second gel was electroblotted onto a PVDF membrane (0.45 micron pore size, Novex) for ~2 hrs at 4° C. using a BioRad Mini-Protean II blotting apparatus and Towbin's methanol (20%) transfer buffer. Blocking of the membrane and antibody incubations were performed according to methods well known in the art. A monoclonal anti-RGS (His)3 antibody, followed by a second rabbit anti-mouse antibody conjugated to HRP (QiaGen), was used to confirm the expression and identity of the BASB010 recombinant protein. Visualization of the anti-His antibody reactive pattern was achieved using either an ABT insoluble substrate or using Hyperfilm with the Amersham ECL chemiluminescence system.

D: Sequence Confirmation.

To further verify that the arabinose-inducible recombinant BASB010 protein being expressed is in the correct open reading frame and not a spurious molecule arising from a cloning artifact (i.e. a frame-shift), the DNA sequence of the cloned insert was determined. The DNA sequence for the M.catarrhalis BASB010 gene was obtained from one strand using conventional asymmetric PCR cycle sequencing methodologies (ABI Prism Dye-Terminator Cycle Sequencing, Perkin-Elmer). Sequencing reactions were programmed with undigested expression plasmid DNA (~0.5 µg/rxn) as a template and appropriate pBADgIII vector-specific and ORF-specific sequencing primers (~3.5 pmol/rxn). In addition to the template and sequencing primer, each sequencing reaction (~20 µl) contained the four different dNTPs (i.e. A, G, C, and T) and the four corresponding ddNTPs (i.e. ddA, ddG, ddC, and ddT) terminator nucleotides; with each terminator being conjugated to one of the four fluorescent dyes, Joe, Tam, Rox, or Fam. Single strand sequencing elongation products were terminated at random positions along the template by the incorporation of the dye-labelled ddNTP terminators. Fluorescent dye-labelled termination products were purified using microcentrifuge size-exclusion chromatography columns (Princeton Genetics), dried under vacuum, suspended in a Template Resuspension Buffer (Perkin-Elmer) for capillary electrophoresis or deionized formamide for PAGE, denatured at 95° C. for ~5 min, and analyzed by high resolution capillary electrophoresis (ABI 310 Automated DNA Sequenator, Perkin-Elmer) or high resolution PAGE (ABI 377 Automated DNA Sequenator) as recommended by the manufacturer. DNA sequence data produced from individual reactions were collected and the relative fluorescent peak intensities analyzed automatically on a PowerMAC computer using ABI Sequence Analysis Software (Perkin-Elmer). Individually autoanalyzed DNA sequences were edited manually for accuracy before being merged into a consensus single strand sequence "string" using AutoAssembler software (Perkin-Elmer). Sequencing determined that the expression plasmid contained the correct sequence in the correct open reading frame.

Example 4

Production of Recombinant BASB010

Purification

Chemicals and Materials

Imidazole, guanidine hydrochloride, Tris (hydroxymethyl), and EDTA (ethylene-diamine tetraacetic acid) biotechnology grade or better were all obtained from Ameresco Chemical, Solon, Ohio. Triton X-100 (t-Octylphenoxypolyethoxy-ethanol), sodium phosphate, monobasic, and Urea were reagent grade or better and obtained from Sigma Chemical Company, St. Louis, Mo. Glacial acetic acid and hydrochloric acid were obtained from Mallincrodt Baker Inc., Phillipsburg, N.J. Methanol was obtained from Fisher Scientific, Fairlawn, N.J. Pefabloc®SC (4-(2-Aminoethyl)-benzenesulfonylfuoride), Complete protease inhibitor cocktail tablets, and PMSF (phenylmethyl-sulfonylfluoride) were obtained from Roche Diagnostics Corporation, Indianapolis, Ind. Bestatin, Pepstatin A, and E-64 protease inhibitor were obtained from Calbiochem, LaJolla, Calif. Dulbecco's Phosphate Buffered Saline(1×PBS) was obtained from Quality Biological, Inc., Gaithersburg, Md. Dulbecco's Phosphate Buffered Saline (10×PBS) was obtained from BioWhittaker, Walkersville, Md. Penta-His Antibody, BSA free was obtained from QiaGen, Valencia, Calif. Peroxidase-conjugated AffiniPure Goat Anti-mouse IgG was obtained from Jackson Immuno Research, West Grove, Pa. AEC single solution was obtained from Zymed, South San Francisco, Calif. All other chemicals were reagent grade or better.

Ni-NTA Superflow resin was obtained from QiaGen Inc., Valencia, Calif. Precast Tris-Glycine 4–20% and 10–20% polyacrylamide gels, all running buffers and solutions, See-Blue Pre-Stained Standards, MultiMark Multi-Colored Standards and PVDF transfer membranes were obtained from Novex, San Diego, Calif. SDS-PAGE Silver Stain kits were obtained from Daiichi Pure Chemicals Company Limited, Tokyo, Japan. Coomassie Stain Solution was obtained from Bio-Rad Laboratories, Hercules, Calif. Acrodisc® PF 0.2 m syringe filters were obtained from Pall Gelman Sciences, Ann Arbor, Mich. GD/X 25 mm disposable syringe filters were obtained from Whatman Inc., Clifton, N.J. Dialysis tubing 8,000 MWCO was obtained from BioDesign Inc. Od New York, Carmal N.Y. BCA Protein Assay Reagents and Snake Skin dialysis tubing 3,500 MWCO were obtained from Pierce Chemical Co., Rockford, Ill.

Extraction Protocol

Cell paste was thawed at room temperature for 30 to 60 minutes. Five to six grams of material was weighed out into a 50 ml disposable centrifuge tube. To this five mls/gram of Guanidine hydrochloride (Gu-HCl) buffer was added (6 M Guanidine hydrochloride, 100 mM Sodium phosphate, monobasic, 10 mM Tris and 0.05% Triton X-100, pH 8.0). Cell paste was resuspended using a PRO300D proscientific homogenizer, at ¾ power for one minute. The extraction mixture was then placed at room temperature with gentle agitation for 60 to 90 minutes. After 60 to 90 minutes the extraction mixture was centrifuged at 15,800×g for 15 minutes (Sorvall RC5C centrifuge, 11,500 rpm). The supernatant (S1) was decanted and saved for additional purification. The pellet (P1) was saved for analysis.

Binding of BASB010 to Nickel-NTA Resin

To the S1 3–4mls of Ni-NTA resin is added. This is then placed at room temperature with gentle agitation for one hour. After one hour the S1/Ni-NTA is packed into an XK16 Pharmacia column. The column is then washed with 1 M Gu-HCl buffer (1 M Guanidine hydrochloride, 100 mM Sodium phosphate, monobasic, 10 mM Tris and 0.05% Triton X-100, pH 8.0). This is then followed by a wash with phosphate buffer (100 mM Sodium phosphate, monobasic, 10 mM Tris and 0.05% TritonX-100, pH 6.3). The protein is then eluted from the column with a 250 mM imidazole buffer (250 mM imidazole, 100 mM Sodium phosphate, monobasic, 10 mM Tris and 0.05% Triton X-100, pH 5.9).

Final Formulation

BASB010 was formulated by dialysis overnight against, three changes of 0.1% Triton X-100 and 1×PBS, pH 7.4, to remove residual Gu-HCl and imidazole. The purified protein was characterized and used to produced antibodies as described below.

Biochemical Characterizations

SDS-PAGE and Western Blot Analysis

The recombinant purified protein was resolved on 4–20% polyacrylamide gels and electrophoretically transferred to PVDF membranes at 100 V for 1 hour as previously described (Thebaine et al. 1979, Proc. Natl. Acad. Sci. USA 76:4350–4354). The PVDF membranes were then pretreated with 25 ml of Dulbecco's phosphate buffered saline containing 5% non-fat dry milk. All subsequent incubations were carried out using this pretreatment buffer.

PVDF membranes were incubated with 25 ml of a 1:500 dilution of preimmune serum or rabbit anti-His immune serum for 1 hour at room temperature. PVDF membranes were then washed twice with wash buffer (20 mM Tris buffer, pH 7.5, containing 150 mM sodium chloride and 0.05% Tween-20). PVDF membranes were incubated with 25 ml of a 1:5000 dilution of peroxidase-labeled goat anti-rabbit IgG (Jackson ImmunoResearch Laboratories, West Grove, Pa.) for 30 minutes at room temperature. PVDF membranes were then washed 4 times with wash buffer, and were developed with 3-amino-9-ethylcarbazole and urea peroxide as supplied by Zymed (San Francisco, Calif.) for 10 minutes each.

Figure 4:
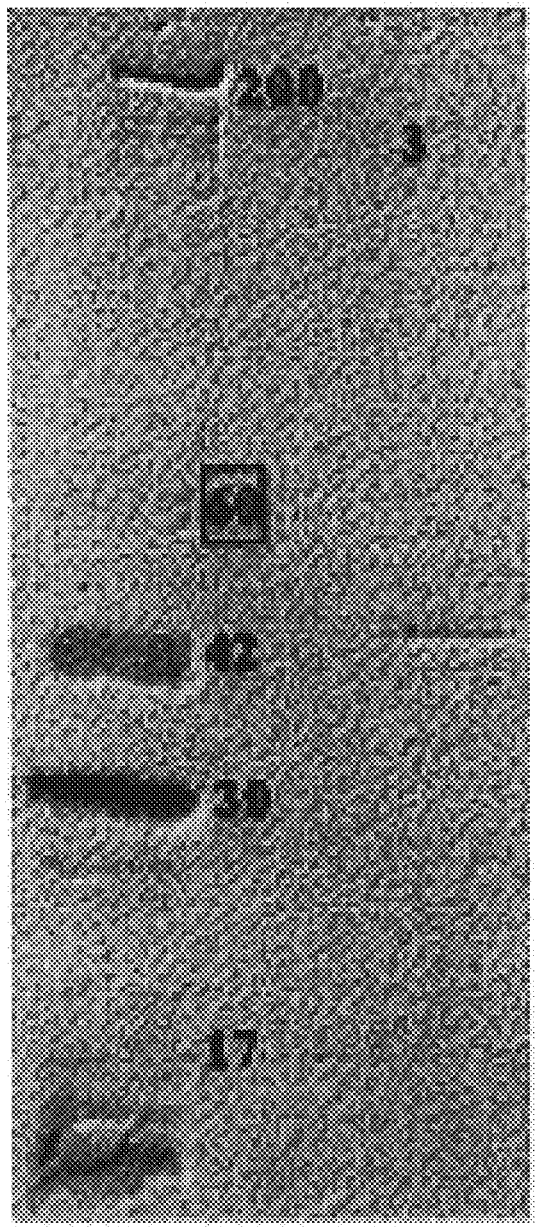
FIG. 4 shows a Western-blot of BASB010 protein probed with tetra-His antibody.

The results of an SDS-PAGE show a protein about 45 kDa purified to greater than 95% (data not shown) and that is reactive to an anti-RGS(His) antibody by western blots (FIG. 4) of the SDS-PAGE.

Protein Sequencing

Amino terminal amino acid sequencing of the purified protein was performed to confirm the production of the correct recombinant protein using well defined chemical protocols on Hewlett-Packard model G1000A sequencer with a model 1090 LC and a Hewlett-Packard model 241 sequencer with a model 1100 LC.

Example 5

Efficacy of BASB010 Vaccine: Enhancement of Lung Clearance of *M. catarrhalis* in Mice The protective capacity of the purified recombinant BASB010 protein was evaluated in a mouse model.

This mouse model is based on the analysis of the lung invasion by *M. catarrhalis* following a standard intranasal challenge to vaccinated mice.

Groups of 6 BALB/c mice (females, 6 weeks old) are immunized subcutaneously with 100 µl of vaccine corresponding to a 10 µg dose and are boosted 2 weeks later. One week after the booster, the mice are challenged by instillation of 50 µl of bacterial suspension ($+/-10^6$ CFU/50 µl) into the left nostril under anaesthesia (mice are anaesthetised with a combination of ketamine and xylazine anaesthetics, 0.24 mg xylazine (Rompun) and 0.8 mg ketamine (Imalgene)/100 µl). Mice are killed 4 hours after challenge and the lungs are removed aseptically and homogenized individually. The log10 weighted mean number of CFU/lung is determined by counting the colonies grown on Mueller-Hinton agar plates after plating of 20 µl of 5 serial dilutions of the homogenate. The arithmetic mean of the log10 weighted mean number of CFU/lung and the standard deviations are calculated for each group.

Results are analysed statistically by applying 1-way ANOVA after assuming equality of variance (checked by Brown and Forsythe's test) and normality (checked using the Shapiro-Wilk test). Differences between groups were analysed using the Dunnet test, Tukey's studentised range test (HSD) and Student-Newman-Keuls test.

In this experiment groups of mice were immunized either with BASB010 adsorbed onto $AlPO_4$ (10 µg of BASB010 onto 100 µg of $AlPO_4$) or with a killed whole cells (kwc) preparation of *M. catarrhalis* strain ATCC 43617 adsorbed onto $AlPO_4$ (5 $10^8$ cells onto 100 µg $AlPO_4$) or with 100 µg $AlPO_4$ without antigen. The mice were challenged with $10^6$ CFU of live *M. catarrhalis* strain ATCC 43617 bacteria.

The log10 weighted mean number of CFU/lung and the standard deviation 4 hours after challenge were calculated for each group.

The kwc preparation and the BASB010 vaccine induced significant lung clearance as compared to the control group.

Deposited Materials

A deposit containing a *Moraxella catarrhalis* Catlin strain has been deposited with the American Type Culture Collection (herein "ATCC") on Jun. 21, 1997 and assigned deposit number 43617. The deposit was described as *Branhamella catarrhalis* (Frosch and Kolle) and is a freeze-dried, 1.5–2.9 kb insert library constructed from *M. catarrhalis* isolate obtained from a transtracheal aspirate of a coal miner with chronic bronchitits. The deposit is described in Antimicrob. Agents Chemother. 21: 506–508 (1982).

The *Moraxella catarrhalis* strain deposit is referred to herein as "the deposited strain" or as "the DNA of the deposited strain."

The deposited strain contains a full length BASB010 gene.

A deposit of the vector pMC-Hly2 consisting of *Moraxella catarrhalis* DNA inserted in pQE30 has been deposited with the American Type Culture Collection (ATCC) on Feb. 12th 1999 and assigned deposit number 207098.

The sequence of the polynucleotides contained in the deposited strain or in the deposited clone, as well as the amino acid sequence of any polypeptide encoded thereby, are controlling in the event of any conflict with any description of sequences herein.

The deposits of the deposited strain/clone have been made under the terms of the Budapest Treaty on the International Recognition of the Deposit of Micro-organisms for Purposes of Patent Procedure. The deposited strains will be irrevocably and without restriction or condition released to the public upon the issuance of a patent. The deposited strains are provided merely as convenience to those of skill in the art and are not an admission that a deposit is required for enablement, such as that required under 35 U.S.C. §112.

SEQUENCE LISTING

<160> NUMBER OF SEQ ID NOS: 10

<210> SEQ ID NO 1
<211> LENGTH: 1176
<212> TYPE: DNA
<213> ORGANISM: Moraxella catarrhalis

<400> SEQUENCE: 1

```
ttgtcttttg tttctatcgc tatttttact gtatcagtag cggctatatt tatcccctca      60
acggcatttg ctgcgtttga gcttggtggc acaccgacca atcttgcgtt attgattttt     120
tttatttgtt tatctttagt cgtgtcattt ttatgctcta tttctgaagc gacattgtta     180
accatgacac cttcttatat tgacacgctt gaagaagata atcccaaagg agcggcactg     240
cttaagagtg tgaaagttga ccacatcgaa aaatcaattt cagcaatttt aacactcaat     300
actgtcgccc atacattagg ttcgcttggt gcaggcgcgc aagcagtgat cgttttggt      360 aatgcatggt ttggggtatt tagcggtgtg atgactttga ttattttgat tggcacagaa     420
attatcccaa aaaccatcgg aacggtatat tggcgacgat ttgctatgcc tgtggcgtat     480
tatgtgcgta caatcaatgt ggcattattg cccgttattt gggtgactga aaaaatttca     540
cgcatgttga ctcgtggcaa tcaagaaatt ggttttaatc gccatgagtt tttggcactt     600
gccaatcaag gggaaagctt ggggcagatg agcgagatgg aaactcgtat tatcaaaaac     660
tctttggcat tgggcatgat taatgtagaa gacattttga cgcctcgttc ggtcgttagt     720
gcgtttgatg aaaatatgac ggtaggcgat gtctttgcca gctatcccaa actacctttg     780
tctcgttttc caatctttga tgaagatttg gataatgcca cagggtttat attaaaatcc     840
gatttactga tcgctaaggc aaatcaagaa attcatacac ccatcaagca atttcggcgt     900
gatatcaact ttgtatttgc caaaatgaaa ctatttgatt tgttggattt gatgttaaaa     960
gagcaagttc acatcgcttt agcggtagga gaatttggtg aggttaaagg attggtgagc    1020
ttagaagatg tgctagaaac cttgcttggt cttgagattg ttgatgaatt tgaccgtgtt    1080
gatgatatgc agattttagc acgccaactc atggataaac gcatggcacg cttgggggca    1140
aaactagaag aagatgcacc gtttgatgaa aagtag                              1176
```

<210> SEQ ID NO 2
<211> LENGTH: 391
<212> TYPE: PRT
<213> ORGANISM: Moraxella catarrhalis

<400> SEQUENCE: 2

```
Met Ser Phe Val Ser Ile Ala Ile Phe Thr Val Ser Val Ala Ala Ile
 1               5                  10                  15

Phe Ile Pro Ser Thr Ala Phe Ala Ala Phe Glu Leu Gly Gly Thr Pro
            20                  25                  30

Thr Asn Leu Ala Leu Leu Ile Phe Phe Ile Cys Leu Ser Leu Val Val
         35                  40                  45

Ser Phe Leu Cys Ser Ile Ser Glu Ala Thr Leu Leu Thr Met Thr Pro
 50                  55                  60

Ser Tyr Ile Asp Thr Leu Glu Glu Asp Asn Pro Lys Gly Ala Ala Leu
 65                  70                  75                  80

Leu Lys Ser Val Lys Val Asp His Ile Glu Lys Ser Ile Ser Ala Ile
                 85                  90                  95

Leu Thr Leu Asn Thr Val Ala His Thr Leu Gly Ser Leu Gly Ala Gly
            100                 105                 110

Ala Gln Ala Val Ile Val Phe Gly Asn Ala Trp Phe Gly Val Phe Ser
        115                 120                 125

Gly Val Met Thr Leu Ile Ile Leu Ile Gly Thr Glu Ile Ile Pro Lys
    130                 135                 140

Thr Ile Gly Thr Val Tyr Trp Arg Arg Phe Ala Met Pro Val Ala Tyr
145                 150                 155                 160

Tyr Val Arg Thr Ile Asn Val Ala Leu Leu Pro Val Ile Trp Val Thr
                165                 170                 175

Glu Lys Ile Ser Arg Met Leu Thr Arg Gly Asn Gln Glu Ile Gly Phe
            180                 185                 190

Asn Arg His Glu Phe Leu Ala Leu Ala Asn Gln Gly Glu Ser Leu Gly
        195                 200                 205

Gln Met Ser Glu Met Glu Thr Arg Ile Ile Lys Asn Ser Leu Ala Leu
    210                 215                 220

Gly Met Ile Asn Val Glu Asp Ile Leu Thr Pro Arg Ser Val Val Ser
225                 230                 235                 240

Ala Phe Asp Glu Asn Met Thr Val Gly Asp Val Phe Ala Ser Tyr Pro
                245                 250                 255

Lys Leu Pro Phe Ser Arg Phe Pro Ile Phe Asp Glu Asp Leu Asp Asn
            260                 265                 270

Ala Thr Gly Phe Ile Leu Lys Ser Asp Leu Leu Ile Ala Lys Ala Asn
        275                 280                 285

Gln Glu Ile His Thr Pro Ile Lys Gln Phe Arg Arg Asp Ile Asn Phe
    290                 295                 300

Val Phe Ala Lys Met Lys Leu Phe Asp Leu Leu Asp Leu Met Leu Lys
305                 310                 315                 320

Glu Gln Val His Ile Ala Leu Ala Val Gly Glu Phe Gly Glu Val Lys
                325                 330                 335

Gly Leu Val Ser Leu Glu Asp Val Leu Glu Thr Leu Gly Leu Glu
            340                 345                 350

Ile Val Asp Glu Phe Asp Arg Val Asp Met Gln Ile Leu Ala Arg
        355                 360                 365

Gln Leu Met Asp Lys Arg Met Ala Arg Leu Gly Ala Lys Leu Glu Glu
    370                 375                 380

Asp Ala Pro Phe Asp Glu Lys
385                 390
```

<210> SEQ ID NO 3

<211> LENGTH: 1176
<212> TYPE: DNA
<213> ORGANISM: Moraxella catarrhalis

<400> SEQUENCE: 3

```
ttgtcttttg tttctatcgc tatttatact gtatcagtag cggctatatt tatcccctca      60
acggcatttg ctgcgtttga gcttggtggc acaccgacca atcttgcgtt attgattttt     120
tttatttgtt tatctttagt cgtgtcattt ttatgctcta tttctgaagc gacattgtta     180
accatgacac cttcttatat tgtcacgctt gaagaagata tcccaaagg agcggcactg     240
cttaagagtg tgaaagttga ccacatcgaa aaatcaattt cagcaatttt aacactcaat     300
actgtcgccc atacattagg ttcgcttggt gcaggcgcgc aagcagtgat cgttttttggt     360
aatgcatggt ttggggtatt tagcggtgtg atgactttga ttattttgat tggcacagaa     420
attatcccaa aaaccatcgg aacgtatat tggcgacgat ttgctatgcc tgtggcgtat     480
tatgtgcgta caatcaatgt ggcattattg cccgttattt gggtgactga aaaaatttca     540
cgcatgttga ctcgtggcaa tcaagaaatt ggttttaatc gccatgagtt tttggcactt     600
gccaatcaag gggaaagctt ggggcagatg agcgagatgg aaactcgtat tatcaaaaac     660
tctttggcat tgggcatgat taatgtagaa gacattttga cgcctcgttc ggtcgttagt     720
gcgtttgatg aaaatatgac ggtaggcgat gtctttgcca gctatcccaa actacctttt     780
tctcgttttc caatctttga tgaagatttg gataatgcca cagggtttat attaaaatcc     840
gatttactga tcgctaaggc aaatcaagaa attcatacac ccatcaagca atgtcggcgt     900
gatatcaact ttgtatttgc caaaatgaaa ctatttgatt tgttggattt gatgttaaaa     960
gagcaagttc acatcgcttt agcggtagga gaatttggtg aggttaaagg attggtgagc    1020
ttagaagatg tgctagaaac cttgcttggt cttgagattg ttgatgaatt tgaccgtgtt    1080
gatgatatgc agattttagc acgccaactc atggataaac gcatggcacg cttgggggca    1140
aaactagaag aagatgcacc gtttgatgaa aagtag                              1176
```

<210> SEQ ID NO 4
<211> LENGTH: 391
<212> TYPE: PRT
<213> ORGANISM: Moraxella catarrhalis

<400> SEQUENCE: 4

Met Ser Phe Val Ser Ile Ala Ile Tyr Thr Val Ser Val Ala Ala Ile
1               5                   10                  15

Phe Ile Pro Ser Thr Ala Phe Ala Phe Glu Leu Gly Gly Thr Pro
            20                  25                  30

Thr Asn Leu Ala Leu Leu Ile Phe Ile Cys Leu Ser Leu Val Val
        35                  40                  45

Ser Phe Leu Cys Ser Ile Ser Glu Ala Thr Leu Thr Met Thr Pro
    50                  55                  60

Ser Tyr Ile Val Thr Leu Glu Glu Asp Asn Pro Lys Gly Ala Ala Leu
65                  70                  75                  80

Leu Lys Ser Val Lys Val Asp His Ile Glu Lys Ser Ile Ser Ala Ile
                85                  90                  95

Leu Thr Leu Asn Thr Val Ala His Thr Leu Gly Ser Leu Gly Ala Gly
            100                 105                 110

Ala Gln Ala Val Ile Val Phe Gly Asn Ala Trp Phe Gly Val Phe Ser
        115                 120                 125

Gly Val Met Thr Leu Ile Ile Leu Ile Gly Thr Glu Ile Ile Pro Lys

```
            130                 135                 140
Thr Ile Gly Thr Val Tyr Trp Arg Arg Phe Ala Met Pro Val Ala Tyr
145                 150                 155                 160

Tyr Val Arg Thr Ile Asn Val Ala Leu Leu Pro Val Ile Trp Val Thr
                165                 170                 175

Glu Lys Ile Ser Arg Met Leu Thr Arg Gly Asn Gln Glu Ile Gly Phe
            180                 185                 190

Asn Arg His Glu Phe Leu Ala Leu Ala Asn Gln Gly Glu Ser Leu Gly
        195                 200                 205

Gln Met Ser Glu Met Glu Thr Arg Ile Ile Lys Asn Ser Leu Ala Leu
    210                 215                 220

Gly Met Ile Asn Val Glu Asp Ile Leu Thr Pro Arg Ser Val Val Ser
225                 230                 235                 240

Ala Phe Asp Glu Asn Met Thr Val Gly Asp Val Phe Ala Ser Tyr Pro
                245                 250                 255

Lys Leu Pro Phe Ser Arg Phe Pro Ile Phe Asp Glu Asp Leu Asp Asn
            260                 265                 270

Ala Thr Gly Phe Ile Leu Lys Ser Asp Leu Leu Ile Ala Lys Ala Asn
        275                 280                 285

Gln Glu Ile His Thr Pro Ile Lys Gln Cys Arg Arg Asp Ile Asn Phe
    290                 295                 300

Val Phe Ala Lys Met Lys Leu Phe Asp Leu Leu Asp Leu Met Leu Lys
305                 310                 315                 320

Glu Gln Val His Ile Ala Leu Ala Val Gly Glu Phe Gly Glu Val Lys
                325                 330                 335

Gly Leu Val Ser Leu Glu Asp Val Leu Glu Thr Leu Leu Gly Leu Glu
            340                 345                 350

Ile Val Asp Glu Phe Asp Arg Val Asp Asp Met Gln Ile Leu Ala Arg
        355                 360                 365

Gln Leu Met Asp Lys Arg Met Ala Arg Leu Gly Ala Lys Leu Glu Glu
    370                 375                 380

Asp Ala Pro Phe Asp Glu Lys
385                 390

<210> SEQ ID NO 5
<211> LENGTH: 1176
<212> TYPE: DNA
<213> ORGANISM: Moraxella catarrhalis

<400> SEQUENCE: 5
ttgtcttttg tttctatcgc tattttact  gtatcagtag cggctatatt tatccctca    60
acggcatttg ctgcgtttga gcttggtggc acaccgacca atcttgcgtt attgattttt   120
tttatttgtt tatctttagt cgtgtcattt ttatgctcta tttctgaagc gacattgtta   180
accatgacac cttcttatat tgacacgctt gaagaagata tcccaaagg agcggcactg    240
cttaagagtg tgaaagttga ccacatcgaa aaatcaattt cagcaatttt aacactcaat   300
actgtcgccc atacattagg ttcgcttggt gcaggcgcgc aagcagtgat cgttttggt    360
aatgcatggt ttgggtatt  tagcggtgtg atgactttga ttattttgat tggcacagaa   420
attatcccaa aaccatcgg  aacggtatat tggcgacgat ttgctatgcc tgtggcgtat   480
tatgtgcgta caatcaatgt ggcattattg cccgttattt gggtgactga aaaaatttca   540
cgcatgttga ctcgtggcaa tcaagaaatt ggttttaatc gccatgagtt tttggcactt   600
gccaatcaag ggaaagcttg gggcagatg  agcgagatgg aaactcgtat tatcaaaaac   660
```

```
tctttggcat tgggcatgat taatgtagaa gacattttga cgcctcgttc ggtcgttagt    720
gcgtttgatg aaaatatgac ggtaggcgat gtctttgcca gctatcccaa actaccttt    780 tctcgttttc caatctttga tgaagatttg gataatgcca cagggtttat attaaaatcc    840
gatttactga tcgctaaggc aaatcaagaa attcatacac ccatcaagca atttcggcgt    900
gatatcaact ttgtatttgc caaaatgaaa ctatttgatt tgttggattt gatgttaaaa    960
gagcaagttc acatcgcttt agcggtagga gaatttggtg aggttaaagg attggtgagc   1020
ttagaagatg tgctagaaac cttgcttggt cttgagattt tgatgaatt tgaccgtgtt   1080 gatgatatgc agattttagc acgccaactc atggataaac gcatggcacg cttgggggca   1140
aaactagaag aagatgcacc gtttgatgaa aagtag                              1176
```

<210> SEQ ID NO 6
<211> LENGTH: 391
<212> TYPE: PRT
<213> ORGANISM: Moraxella catarrhalis

<400> SEQUENCE: 6

```
Met Ser Phe Val Ser Ile Ala Ile Phe Thr Val Ser Val Ala Ala Ile
 1               5                  10                  15

Phe Ile Pro Ser Thr Ala Phe Ala Ala Phe Glu Leu Gly Gly Thr Pro
            20                  25                  30

Thr Asn Leu Ala Leu Leu Ile Phe Phe Ile Cys Leu Ser Leu Val Val
        35                  40                  45

Ser Phe Leu Cys Ser Ile Ser Glu Ala Thr Leu Leu Thr Met Thr Pro
    50                  55                  60

Ser Tyr Ile Asp Thr Leu Glu Glu Asp Asn Pro Lys Gly Ala Ala Leu
65                  70                  75                  80

Leu Lys Ser Val Lys Val Asp His Ile Glu Lys Ser Ile Ser Ala Ile
                85                  90                  95

Leu Thr Leu Asn Thr Val Ala His Thr Leu Gly Ser Leu Gly Ala Gly
            100                 105                 110

Ala Gln Ala Val Ile Val Phe Gly Asn Ala Trp Phe Gly Val Phe Ser
        115                 120                 125

Gly Val Met Thr Leu Ile Ile Leu Ile Gly Thr Glu Ile Ile Pro Lys
    130                 135                 140

Thr Ile Gly Thr Val Tyr Trp Arg Arg Phe Ala Met Pro Val Ala Tyr
145                 150                 155                 160

Tyr Val Arg Thr Ile Asn Val Ala Leu Leu Pro Val Ile Trp Val Thr
                165                 170                 175

Glu Lys Ile Ser Arg Met Leu Thr Arg Gly Asn Gln Glu Ile Gly Phe
            180                 185                 190

Asn Arg His Glu Phe Leu Ala Leu Ala Asn Gln Gly Glu Ser Leu Gly
        195                 200                 205

Gln Met Ser Glu Met Glu Thr Arg Ile Ile Lys Asn Ser Leu Ala Leu
    210                 215                 220

Gly Met Ile Asn Val Glu Asp Ile Leu Thr Pro Arg Ser Val Val Ser
225                 230                 235                 240

Ala Phe Asp Glu Asn Met Thr Val Gly Asp Val Phe Ala Ser Tyr Pro
                245                 250                 255

Lys Leu Pro Phe Ser Arg Phe Pro Ile Phe Asp Glu Asp Leu Asp Asn
            260                 265                 270

Ala Thr Gly Phe Ile Leu Lys Ser Asp Leu Leu Ile Ala Lys Ala Asn
```

```
                   275                 280                 285
Gln Glu Ile His Thr Pro Ile Lys Gln Phe Arg Arg Asp Ile Asn Phe
    290                 295                 300

Val Phe Ala Lys Met Lys Leu Phe Asp Leu Leu Asp Leu Met Leu Lys
305                 310                 315                 320

Glu Gln Val His Ile Ala Leu Ala Val Gly Glu Phe Gly Glu Val Lys
                325                 330                 335

Gly Leu Val Ser Leu Glu Asp Val Leu Glu Thr Leu Leu Gly Leu Glu
                340                 345                 350

Ile Val Asp Glu Phe Asp Arg Val Asp Met Gln Ile Leu Ala Arg
                355                 360                 365

Gln Leu Met Asp Lys Arg Met Ala Arg Leu Gly Ala Lys Leu Glu Glu
    370                 375                 380

Asp Ala Pro Phe Asp Glu Lys
385                 390

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide

<400> SEQUENCE: 7
ccaaaatgtg gcaaatttgt c                                              21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide

<400> SEQUENCE: 8
cttaaaacag aacgggtgct g                                              21

<210> SEQ ID NO 9
<211> LENGTH: 41
<212> TYPE: DNA
<213> ORGANISM: Artificial Sequence
<220> FEATURE:
<223> OTHER INFORMATION: Oligonucleotide

<400> SEQUENCE: 9
atccagaggg ccatggcgtt tgagcttggt ggcacaccga c                        41

<210> SEQ ID NO 10
<211> LENGTH: 42
<212> TYPE: DNA
<213> ORGANISM: Artificial Sequence
<220> FEATURE:
<223> OTHER INFORMATION: Oligonucleotide

<400> SEQUENCE: 10
atccagaggt tctagaccct tttcatcaaa cggtgcatct tc                       42
```

What is claimed is:

1. An isolated polypeptide comprising a member selected from the group consisting of (a) a amino acid sequence matching one of SEQ ID NOs:2, 4, or 6; and (b) an immunogenic polypeptide comprising a fragment sequence of at least 15 amino acids that matches an aligned contiguous segment of one of SEQ ID NOs: SEQ ID NOs:2, 4, or 6; selected from the following contiguous segments thereof: 1–15; 2–16; 3–17; 4–18; 5–19; 6–20; 7–21; 8–22; 9–23; 10–24; 11–25;

12–26; 13–27; 14–28; 15–29; 16–30; 17–31; 18–32; 19–33; 20–34; 21–35; 22–36; 23–37; 24–38; 25–39; 26–40; 27–41; 28–42; 29–43; 30–44; 31–45; 32–46; 33–47; 34–48; 35–49; 36–50; 37–51; 38–52; 39–53; 40–54; 41–55; 42–56; 43–57; 44–58; 45–59; 46–60; 47–61; 48–62; 49–63; 50–64; 51–65; 52–66; 53–67; 54–68; 55–69; 56–70; 57–71; 58–72, 59–73; 60–74; 61–75; 62–76; 63–77; 64–78; 65–79; 66–80; 67–81; 68–82; 69–83; 70–84; 71–85; 72–86; 73–87; 74–88; 75–89; 76–90; 77–91; 78–92; 79–93; 80–94; 81–95; 82–96; 83–97; 84–98; 85–99; 86–100; 87–101; 88–102; 89–103; 90–104; 91–105; 92–106; 93–107; 94–108; 95–109; 96–110; 97–111; 98–112; 99–113; 100–114; 101–115; 102–116; 103–117; 104–118; 105–119; 106–120; 107–121; 108–122; 109–123; 110–124; 111–125; 112–126; 113–127; 114–128; 115–129; 116–130; 117–131; 118–132; 119–133; 120–134; 121–135; 122–136; 123–137; 124–138; 125–139; 126–140; 127–141; 128–142; 129–143; 130–144; 131–145; 132–146; 133–147; 134–148; 135–149; 136–150; 137–151; 138–152; 139–153; 140–154; 141–155; 142–156; 143–157; 144–158; 145–159; 146–160; 147–161; 148–162; 149–163; 150–164; 151–165; 152–166; 153–167; 154–168; 155–169; 156–170; 157–171; 158–172; 159–173; 160–174; 161–175; 162–176; 163–177; 164–178; 165–179; 166–180; 167–181; 168–182; 169–183; 170–184; 171–185; 172–186; 173–187; 174–188; 175–189; 176–190; 177–191; 178–192; 179–193; 180–194; 181–195; 182–196; 183–197; 184–198; 185–199; 186–200; 187–201; 188–202; 189–203; 190–204; 191–205; 192–206; 193–207; 194–208; 195–209; 196–210; 197–211; 198–212; 199–213; 200–214; 201–215; 202–216; 203–217; 204–218; 205–219; 206–220; 207–221; 208–222; 209–223; 210–224; 211–225; 212–226; 213–227; 214–228; 215–229; 216–230; 217–231; 218–232; 219–233; 220–234; 221–235; 222–236; 223–237; 224–238; 225–239; 226–240; 227–241; 228–242; 229–243; 230–244; 231–245; 232–246; 233–247; 234–248; 235–249; 236–250; 237–251; 238–252; 239–253; 240–254; 241–255; 242–256; 243–257; 244–258; 245–259; 246–260; 247–261; 248–262; 249–263; 240–264; 251–265; 252–266; 253–267; 254–268; 255–269; 256–270; 257–271; 258–272; 259–273; 260–274; 261–275; 262–276; 263–277; 264–278; 265–279; 266–280; 267–281; 268–282; 269–283; 270–284; 271–285; 272–286; 273–287; 274–288; 275–289; 276–290; 277–291; 278–292; 279–293; 280–294; 281–295; 282–296; 283–297; 284–298; 285–299; 286–300; 287–301; 288–302; 289–303; 290–304; 291–305; 292–306; 293–307; 294–308; 295–309; 296–310; 297–311; 298–312; 299–313; 300–314; 301–315; 302–316; 303–317; 304–318; 305–319; 306–320; 307–321; 308–322; 309–323; 310–324; 311–325; 312–326; 313–327; 314–328; 315–329; 316–330; 317–331; 318–332; 319–333; 320–334; 321–335; 322–336; 323–337; 324–338; 325–339; 326–340; 327–341; 328–342; 329–343; 330–344; 331–345; 332–346; 333–347; 334–348; 335–349; 336–350; 337–351; 338–352; 339–353; 340–354; 341–355; 342–356; 343–357; 344–358; 345–359; 346–360; 347–361; 348–362; 349–363; 350–364; 351–365; 352–366; 353–367; 354–368; 355–369; 356–370; 357–371; 358–372; 359–373; 360–374; 361–375; 362–376; 363–377; 364–378; 365–379; 366–380; 367–381; 368–382; 369–383; 370–384; 371–385; 372–386; 373–387; 374–388; 375–389; 376–390; 377–391;

wherein the isolated polypeptide, when administered to a subject in a composition which can include an adjuvant, or a carrier coupled to the polypeptide, induces an antibody or T-cell immune response to a polypeptide having the sequence of one of SEQ ID NOs:2, 4, or 6.

2. The isolated polypeptide of claim 1, wherein the polypeptide is according to (a).

3. The isolated polypeptide of claim 1 wherein the isolated polypeptide of (a) consists of one of SEQ ID NOs:2, 4, and 6.

4. The isolated polypeptide of claim 1, wherein the polypeptide is according to (b).

5. A fusion protein comprising the isolated polypeptide of claim 1 and a polypeptide selected to:

(a) provide T helper epitopes;

(b) facilitate purification from a recombinant expression system, or (c) stabilize the isolated polypeptide during recombinant expression.

6. An immunogenic composition comprising the polypeptide of claim 1 and a pharmaceutically acceptable carrier.

* * * * *